US008905977B2

United States Patent
Shelton et al.

(10) Patent No.: US 8,905,977 B2
(45) Date of Patent: *Dec. 9, 2014

(54) SURGICAL STAPLING INSTRUMENT HAVING AN ELECTROACTIVE POLYMER ACTUATED MEDICAL SUBSTANCE DISPENSER

(75) Inventors: Frederick E. Shelton, Hillsboro, OH (US); Joseph C. Hueil, Loveland, OH (US); Jerome R. Morgan, Cincinnati, OH (US)

(73) Assignee: Ethicon Endo-Surgery, Inc.

( * ) Notice: Subject to any disclaimer, the term of this patent is extended or adjusted under 35 U.S.C. 154(b) by 1914 days.

This patent is subject to a terminal disclaimer.

(21) Appl. No.: 11/141,753

(22) Filed: Jun. 1, 2005

(65) Prior Publication Data

US 2006/0025813 A1 Feb. 2, 2006

Related U.S. Application Data

(60) Provisional application No. 60/591,694, filed on Jul. 28, 2004.

(51) Int. Cl.
*A61M 5/00* (2006.01)
*A61B 17/072* (2006.01)
*A61B 17/00* (2006.01)
*A61B 17/29* (2006.01)

(52) U.S. Cl.
CPC . *A61B 17/07207* (2013.01); *A61B 2017/00398* (2013.01); *A61B 2017/00871* (2013.01); *A61B 2017/2912* (2013.01)
USPC ............................. 604/246; 604/207; 604/131

(58) Field of Classification Search
USPC .................. 604/246, 207, 131; 606/205, 139, 606/219–220, 213–214; 227/175.1–182.1
See application file for complete search history.

(56) References Cited

U.S. PATENT DOCUMENTS

| 2,711,461 A | 6/1955 | Happe |
| 3,490,675 A | 1/1970 | Green et al. |

(Continued)

FOREIGN PATENT DOCUMENTS

| CA | 2458946 | 3/2003 |
| CA | 2477181 | 4/2004 |

(Continued)

OTHER PUBLICATIONS

EPO Search Report, Application No. 06255058.7, Jan. 31, 2007, pp. 1-3.

(Continued)

*Primary Examiner* — Kevin C Sirmons
*Assistant Examiner* — Phillip Gray

(57) ABSTRACT

A surgical stapling and severing instrument enables minimally invasive surgical procedures by having upper and lower jaws (i.e., anvil and staple channel) that are positioned with an elongate shaft and handle through a surgical opening, and in particular through a cannula of a trocar. A pair of fluid bladders (lift bags) are positioned in the staple channel beneath a proximally projecting lever tray so that transfer of fluid from the handle causes closing and clamping of the anvil. The bi-directional fluid control may be mechanically produced at the handle or by activating an electroactive polymer actuator. Once firing is sensed, an EAP plunger in a medical substance syringe inserted into the elongate shaft is activated to dispense a medical substance (e.g., anesthetics, adhesives, cauterizing substances, antibiotics, etc.) and is guided along a firing bar to a cutting surface of an E-beam placing the substance on tissue as severed.

17 Claims, 9 Drawing Sheets

(56) References Cited

U.S. PATENT DOCUMENTS

| | | |
|---|---|---|
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| RE28,932 E | 8/1976 | Noiles et al. |
| 4,060,089 A | 11/1977 | Noiles |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,434,796 A | 3/1984 | Karapetian et al. |
| 4,473,077 A | 9/1984 | Noiles et al. |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,522,327 A | 6/1985 | Korthoff et al. |
| 4,530,453 A | 7/1985 | Green |
| 4,543,090 A | 9/1985 | McCoy |
| 4,554,064 A | 11/1985 | McClintock et al. |
| 4,566,620 A | 1/1986 | Green et al. |
| 4,573,622 A | 3/1986 | Green et al. |
| 4,580,712 A | 4/1986 | Green |
| 4,601,705 A | 7/1986 | McCoy |
| 4,610,383 A | 9/1986 | Rothfuss et al. |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,753,223 A | 6/1988 | Bremer |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,841 A | 4/1989 | Justus |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,890,613 A | 1/1990 | Golden et al. |
| 4,892,545 A | 1/1990 | Day et al. |
| 4,932,960 A | 6/1990 | Green et al. |
| 4,941,623 A | 7/1990 | Pruitt |
| 4,944,443 A | 7/1990 | Oddsen et al. |
| 4,986,808 A | 1/1991 | Broadwin et al. |
| 4,988,334 A | 1/1991 | Homlein et al. |
| 5,015,227 A | 5/1991 | Broadwin et al. |
| 5,024,652 A | 6/1991 | Dumenek et al. |
| 5,031,814 A | 7/1991 | Thompkins et al. |
| 5,040,715 A | 8/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,156,614 A | 10/1992 | Green et al. |
| 5,158,567 A | 10/1992 | Green |
| 5,171,249 A | 12/1992 | Stefanchik et al. |
| 5,188,102 A | 2/1993 | Idemoto et al. |
| 5,190,517 A | 3/1993 | Zieve et al. |
| 5,202,914 A | 4/1993 | Kim et al. |
| 5,207,697 A | 5/1993 | Carusillo et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,258,012 A | 11/1993 | Luscombe et al. |
| 5,263,629 A | 11/1993 | Trumbull et al. |
| 5,282,829 A | 2/1994 | Hermes |
| 5,290,240 A | 3/1994 | Horres, Jr. |
| 5,304,204 A | 4/1994 | Bregen |
| 5,312,023 A | 5/1994 | Green et al. |
| 5,312,329 A | 5/1994 | Beaty et al. |
| 5,330,087 A | 7/1994 | Murray et al. |
| 5,330,502 A | 7/1994 | Hassler et al. |
| 5,342,395 A | 8/1994 | Jarrett et al. |
| 5,342,396 A | 8/1994 | Cook |
| 5,350,400 A | 9/1994 | Esposito et al. |
| 5,352,238 A | 10/1994 | Green et al. |
| 5,358,510 A | 10/1994 | Luscombe et al. |
| 5,366,479 A | 11/1994 | McGarry et al. |
| 5,372,124 A | 12/1994 | Takayama et al. |
| 5,387,194 A | 2/1995 | Williams et al. |
| 5,389,098 A | 2/1995 | Tsuruta et al. |
| 5,391,180 A | 2/1995 | Tovey et al. |
| 5,395,312 A | 3/1995 | Desai |
| 5,397,046 A | 3/1995 | Savage et al. |
| 5,397,324 A | 3/1995 | Carroll et al. |
| 5,399,256 A | 3/1995 | Bohs et al. |
| 5,403,312 A | 4/1995 | Yates et al. |
| 5,405,072 A | 4/1995 | Zlock et al. |
| 5,413,267 A | 5/1995 | Solyntjes et al. |
| 5,413,268 A | 5/1995 | Green et al. |
| 5,413,272 A | 5/1995 | Green et al. |
| 5,425,745 A | 6/1995 | Green et al. |
| 5,431,668 A | 7/1995 | Burbank, III et al. |
| 5,441,193 A | 8/1995 | Gravener |
| 5,445,304 A | 8/1995 | Plyley et al. |
| 5,465,895 A | 11/1995 | Knodel et al. |
| 5,468,250 A | 11/1995 | Paraschac et al. |
| 5,476,479 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,484,095 A | 1/1996 | Green et al. |
| 5,484,398 A | 1/1996 | Stoddard |
| 5,487,499 A | 1/1996 | Sorrentino et al. |
| 5,497,933 A | 3/1996 | DeFonzo et al. |
| 5,503,638 A | 4/1996 | Cooper et al. |
| 5,505,363 A | 4/1996 | Green et al. |
| 5,507,426 A | 4/1996 | Young et al. |
| 5,520,787 A | 5/1996 | Hanagan et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,542,594 A | 8/1996 | McKean et al. |
| 5,549,628 A | 8/1996 | Cooper et al. |
| 5,554,169 A | 9/1996 | Green et al. |
| 5,555,555 A | 9/1996 | Sato et al. |
| 5,556,416 A | 9/1996 | Clark et al. |
| 5,562,239 A | 10/1996 | Boiarski et al. |
| 5,562,241 A | 10/1996 | Knodel et al. |
| 5,564,615 A | 10/1996 | Bishop et al. |
| 5,577,654 A | 11/1996 | Bishop |
| 5,584,425 A | 12/1996 | Savage et al. |
| 5,588,579 A | 12/1996 | Schnut et al. |
| 5,592,668 A | 1/1997 | Harding et al. |
| 5,599,329 A | 2/1997 | Gabbay |
| 5,601,224 A | 2/1997 | Bishop et al. |
| 5,601,582 A | 2/1997 | Shelton, IV et al. |
| 5,602,914 A | 2/1997 | Andreini et al. |
| 5,607,094 A | 3/1997 | Clark et al. |
| 5,609,285 A | 3/1997 | Grant |
| 5,618,303 A | 4/1997 | Marlow et al. |
| 5,624,452 A | 4/1997 | Yates |
| 5,628,446 A | 5/1997 | Geiste et al. |
| 5,630,539 A | 5/1997 | Plyley et al. |
| 5,634,584 A | 6/1997 | Okorocha et al. |
| 5,639,008 A | 6/1997 | Gallagher et al. |
| 5,651,491 A | 7/1997 | Heaton et al. |
| 5,653,373 A | 8/1997 | Green et al. |
| 5,653,721 A | 8/1997 | Knodel et al. |
| 5,661,887 A | 9/1997 | Byrne et al. |
| 5,662,258 A | 9/1997 | Knodel et al. |
| 5,665,285 A | 9/1997 | Hattori et al. |

(56) References Cited

U.S. PATENT DOCUMENTS

| | | | |
|---|---|---|---|
| 5,667,517 A | 9/1997 | Hooven | |
| 5,667,527 A | 9/1997 | Cook | |
| 5,669,918 A | 9/1997 | Balazs | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,688,270 A | 11/1997 | Yates et al. | |
| 5,692,668 A | 12/1997 | Schulze et al. | |
| 5,693,042 A | 12/1997 | Boiarski et al. | |
| 5,695,524 A | 12/1997 | Kelley et al. | |
| 5,702,409 A | 12/1997 | Rayburn et al. | |
| 5,704,534 A | 1/1998 | Huitema et al. | |
| 5,709,334 A | 1/1998 | Sorrentino et al. | |
| 5,711,472 A | 1/1998 | Bryan | |
| 5,715,987 A | 2/1998 | Kelley et al. | |
| 5,716,366 A | 2/1998 | Yates | |
| 5,725,554 A | 3/1998 | Simon et al. | |
| 5,730,758 A | 3/1998 | Allgeyer | |
| 5,732,871 A | 3/1998 | Clark et al. | |
| 5,735,445 A | 4/1998 | Vidal et al. | |
| 5,749,893 A | 5/1998 | Vidal et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,769,892 A | 6/1998 | Kingwell | |
| 5,779,130 A | 7/1998 | Alesi et al. | |
| 5,782,396 A | 7/1998 | Mastri et al. | |
| 5,782,859 A | 7/1998 | Nicholas et al. | |
| 5,792,165 A | 8/1998 | Klieman et al. | |
| 5,797,536 A | 8/1998 | Smith et al. | |
| 5,797,537 A | 8/1998 | Oberlin et al. | |
| 5,810,855 A | 9/1998 | Rayburn et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,839,639 A | 11/1998 | Sauer et al. | |
| 5,855,565 A | 1/1999 | Bar-Cohen et al. | |
| 5,865,361 A | 2/1999 | Milliman et al. | |
| 5,868,744 A | 2/1999 | Willmen | |
| 5,876,401 A | 3/1999 | Schulze et al. | |
| 5,901,895 A | 5/1999 | Heaton et al. | |
| 5,902,312 A | 5/1999 | Frater et al. | |
| 5,908,427 A | 6/1999 | McKean et al. | |
| 5,911,353 A | 6/1999 | Bolanos et al. | |
| 5,918,791 A | 7/1999 | Sorrentino et al. | |
| 5,931,847 A | 8/1999 | Bittner et al. | |
| 5,941,442 A | 8/1999 | Geiste et al. | |
| 5,954,259 A | 9/1999 | Viola et al. | |
| 5,959,852 A | 9/1999 | Deloy et al. | |
| 5,964,774 A | 10/1999 | McKean et al. | |
| 5,972,165 A | 10/1999 | Sethna et al. | |
| 6,010,054 A | 1/2000 | Johnson et al. | |
| 6,032,849 A | 3/2000 | Mastri et al. | |
| 6,033,427 A * | 3/2000 | Lee | 606/213 |
| 6,063,097 A | 5/2000 | Oi et al. | |
| 6,079,606 A | 6/2000 | Milliman et al. | |
| 6,083,242 A | 7/2000 | Cook | |
| 6,099,551 A | 8/2000 | Gabbay | |
| 6,102,271 A | 8/2000 | Longo et al. | |
| 6,109,500 A | 8/2000 | Alli et al. | |
| 6,126,058 A | 10/2000 | Adams et al. | |
| 6,171,330 B1 | 1/2001 | Benchetrit | |
| 6,193,129 B1 | 2/2001 | Bittner et al. | |
| 6,202,914 B1 | 3/2001 | Geiste et al. | |
| 6,214,028 B1 | 4/2001 | Yoon et al. | |
| 6,228,084 B1 | 5/2001 | Kirwan, Jr. | |
| 6,241,139 B1 | 6/2001 | Milliman | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,270,508 B1 | 8/2001 | Klieman et al. | |
| 6,302,311 B1 | 10/2001 | Adams et al. | |
| 6,309,403 B1 | 10/2001 | Minor et al. | |
| 6,315,184 B1 | 11/2001 | Whitman | |
| 6,330,965 B1 | 12/2001 | Milliman et al. | |
| 6,358,224 B1 | 3/2002 | Tims et al. | |
| 6,387,113 B1 | 5/2002 | Hawkins et al. | |
| 6,387,114 B2 | 5/2002 | Adams | |
| 6,398,797 B2 | 6/2002 | Bombard et al. | |
| RE37,814 E | 8/2002 | Allgeyer | |
| 6,440,146 B2 | 8/2002 | Nicholas et al. | |
| 6,443,973 B1 | 9/2002 | Whitman | |
| 6,488,196 B1 | 12/2002 | Fenton, Jr. | |
| 6,488,197 B1 * | 12/2002 | Whitman | 227/180.1 |
| 6,491,201 B1 | 12/2002 | Whitman | |
| 6,494,896 B1 * | 12/2002 | D'Alessio et al. | 606/213 |
| 6,503,257 B2 | 1/2003 | Grant et al. | |
| 6,503,259 B2 | 1/2003 | Huzel et al. | |
| 6,505,768 B2 | 1/2003 | Whitman | |
| 6,514,237 B1 | 2/2003 | Maseda | |
| 6,517,565 B1 | 2/2003 | Whitman et al. | |
| 6,517,566 B1 | 2/2003 | Hovland et al. | |
| 6,545,384 B1 * | 4/2003 | Pelrine et al. | 310/309 |
| 6,577,899 B2 | 6/2003 | Lebel et al. | |
| 6,583,533 B2 | 6/2003 | Kornbluh et al. | |
| 6,586,859 B2 | 7/2003 | Kornbluh et al. | |
| 6,595,852 B2 | 7/2003 | Wang | |
| 6,601,749 B2 | 8/2003 | Sullivan et al. | |
| 6,616,686 B2 | 9/2003 | Coleman et al. | |
| 6,629,630 B2 | 10/2003 | Adams | |
| 6,629,988 B2 | 10/2003 | Weadock | |
| 6,652,521 B2 | 11/2003 | Schulze | |
| 6,656,193 B2 | 12/2003 | Grant et al. | |
| 6,667,825 B2 | 12/2003 | Lu et al. | |
| 6,669,073 B2 | 12/2003 | Milliman et al. | |
| 6,681,979 B2 | 1/2004 | Whitman | |
| 6,695,199 B2 | 2/2004 | Whitman | |
| 6,698,643 B2 | 3/2004 | Whitman | |
| 6,699,245 B2 | 3/2004 | Dinger et al. | |
| 6,716,232 B1 | 4/2004 | Vidal et al. | |
| 6,716,233 B1 | 4/2004 | Whitman | |
| 6,722,552 B2 | 4/2004 | Fenton, Jr. | |
| 6,740,079 B1 | 5/2004 | Eggers et al. | |
| 6,755,338 B2 | 6/2004 | Hahnen et al. | |
| 6,770,027 B2 | 8/2004 | Banik et al. | |
| 6,786,382 B1 | 9/2004 | Hoffman | |
| 6,805,273 B2 | 10/2004 | Bilotti et al. | |
| 6,830,174 B2 | 12/2004 | Hillstead et al. | |
| 6,835,173 B2 | 12/2004 | Couvillon, Jr. | |
| 6,840,246 B2 | 1/2005 | Downing | |
| RE38,708 E | 3/2005 | Bolanos et al. | |
| 6,866,178 B2 | 3/2005 | Adams et al. | |
| 6,874,669 B2 | 4/2005 | Adams et al. | |
| 6,905,057 B2 | 6/2005 | Swayze et al. | |
| 6,913,579 B2 | 7/2005 | Truckai et al. | |
| 6,923,804 B2 | 8/2005 | Eggers et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,851 B2 | 11/2005 | Heinrich | |
| 6,959,852 B2 | 11/2005 | Shelton, IV et al. | |
| 6,960,163 B2 | 11/2005 | Ewers et al. | |
| 6,964,363 B2 | 11/2005 | Wales et al. | |
| 6,969,395 B2 | 11/2005 | Eskuri | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,988,649 B2 | 1/2006 | Shelton, IV et al. | |
| 7,000,819 B2 | 2/2006 | Swayze et al. | |
| 7,018,390 B2 | 3/2006 | Turovskiy et al. | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,055,731 B2 | 6/2006 | Shelton, IV et al. | |
| 7,056,330 B2 | 6/2006 | Gayton | |
| 7,063,671 B2 | 6/2006 | Couvillon | |
| 7,063,699 B2 | 6/2006 | Hess et al. | |
| 7,074,217 B2 | 7/2006 | Strul et al. | |
| 7,077,856 B2 | 7/2006 | Whitman | |
| 7,083,075 B2 | 8/2006 | Swayze et al. | |
| 7,108,709 B2 | 9/2006 | Cummins | |
| 7,111,769 B2 | 9/2006 | Wales et al. | |

(56) References Cited

U.S. PATENT DOCUMENTS

| | | |
|---|---|---|
| 7,112,214 B2 | 9/2006 | Peterson et al. |
| 7,114,642 B2 | 10/2006 | Whitman |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,648 B2 | 12/2006 | Lin |
| 7,147,650 B2 | 12/2006 | Lee |
| 7,156,863 B2 | 1/2007 | Sonnenschein et al. |
| 7,159,750 B2 | 1/2007 | Racenet et al. |
| 7,182,239 B1 | 2/2007 | Myers |
| 7,188,758 B2 | 3/2007 | Viola et al. |
| 7,208,005 B2 | 4/2007 | Frecker et al. |
| 7,208,421 B2 | 4/2007 | Sakamoto et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,235,089 B1 | 6/2007 | McGuckin, Jr. |
| 7,237,708 B1 | 7/2007 | Guy et al. |
| 7,238,195 B2 * | 7/2007 | Viola ............................ 606/219 |
| 7,246,734 B2 | 7/2007 | Shelton, IV |
| 7,278,563 B1 | 10/2007 | Green |
| 7,300,450 B2 | 11/2007 | Vleugels et al. |
| 7,303,106 B2 | 12/2007 | Milliman et al. |
| 7,303,108 B2 | 12/2007 | Shelton, IV |
| 7,320,700 B2 | 1/2008 | Cooper et al. |
| 7,328,828 B2 | 2/2008 | Ortiz et al. |
| 7,334,717 B2 | 2/2008 | Rethy et al. |
| 7,338,509 B2 | 3/2008 | Mattison |
| 7,338,513 B2 | 3/2008 | Lee et al. |
| 7,343,920 B2 | 3/2008 | Toby et al. |
| 7,354,447 B2 * | 4/2008 | Shelton et al. ............... 606/219 |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 * | 10/2008 | Viola ............................ 606/219 |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,473,263 B2 | 1/2009 | Johnston et al. |
| 7,481,347 B2 | 1/2009 | Roy |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,517,356 B2 * | 4/2009 | Heinrich ........................ 606/219 |
| 7,546,940 B2 | 6/2009 | Milliman et al. |
| 7,549,563 B2 | 6/2009 | Mather et al. |
| 7,549,564 B2 | 6/2009 | Boudreaux |
| 7,556,185 B2 | 7/2009 | Viola |
| 7,556,647 B2 | 7/2009 | Drews et al. |
| 7,559,450 B2 | 7/2009 | Wales et al. |
| 7,559,452 B2 * | 7/2009 | Wales et al. ................ 227/176.1 |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton et al. |
| 7,624,902 B2 | 12/2009 | Marczyk et al. |
| 7,631,793 B2 | 12/2009 | Rethy et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,686,826 B2 | 3/2010 | Lee et al. |
| 7,695,485 B2 | 4/2010 | Whitman et al. |
| 7,699,204 B2 | 4/2010 | Viola |
| 7,708,180 B2 | 5/2010 | Murray et al. |
| 7,708,758 B2 | 5/2010 | Lee et al. |
| 7,717,312 B2 | 5/2010 | Beetel |
| 7,717,313 B2 | 5/2010 | Criscuolo et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,780,054 B2 | 8/2010 | Wales et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,426 B2 | 11/2010 | Racenet et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |

(56) References Cited

U.S. PATENT DOCUMENTS

| | | | |
|---|---|---|---|
| 7,845,533 B2 | 12/2010 | Marczyk et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,892,245 B2 | 2/2011 | Liddicoat et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,221 B2 | 3/2011 | Viola et al. |
| 7,913,891 B2 | 3/2011 | Doll et al. |
| 7,918,377 B2 | 4/2011 | Fuchs et al. |
| 7,922,061 B2 | 4/2011 | Shelton, IV et al. |
| 7,922,063 B2 | 4/2011 | Zemlok et al. |
| 7,926,691 B2 | 4/2011 | Viola et al. |
| 7,934,630 B2 | 5/2011 | Shelton, IV et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,050 B2 | 6/2011 | Smith et al. |
| 7,959,051 B2 | 6/2011 | Smith et al. |
| 7,966,799 B2 | 6/2011 | Morgan et al. |
| 7,967,180 B2 | 6/2011 | Scirica |
| 7,980,443 B2 | 7/2011 | Scheib et al. |
| 7,992,757 B2 | 8/2011 | Wheeler et al. |
| 8,002,795 B2 | 8/2011 | Beetel |
| 8,011,551 B2 | 9/2011 | Marczyk et al. |
| 8,011,555 B2 | 9/2011 | Tarinelli et al. |
| 8,016,855 B2 | 9/2011 | Whitman et al. |
| 8,016,858 B2 | 9/2011 | Whitman |
| 8,020,743 B2 | 9/2011 | Shelton, IV et al. |
| 8,025,199 B2 | 9/2011 | Whitman et al. |
| 8,028,883 B2 | 10/2011 | Stopek |
| 8,034,077 B2 | 10/2011 | Smith et al. |
| 8,043,328 B2 | 10/2011 | Hahnen et al. |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,097,017 B2 | 1/2012 | Viola |
| 8,113,410 B2 | 2/2012 | Hall et al. |
| 8,123,103 B2 | 2/2012 | Milliman |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,172,120 B2 | 5/2012 | Boyden et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,241,322 B2 | 8/2012 | Whitman et al. |
| 8,245,899 B2 | 8/2012 | Swensgard et al. |
| 8,256,654 B2 | 9/2012 | Bettuchi et al. |
| 8,267,300 B2 | 9/2012 | Boudreaux |
| 8,292,155 B2 | 10/2012 | Shelton, IV et al. |
| 8,308,040 B2 | 11/2012 | Huang et al. |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,333,313 B2 | 12/2012 | Boudreaux |
| 8,348,129 B2 | 1/2013 | Bedi et al. |
| 8,348,131 B2 | 1/2013 | Omaits et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,299 B2 | 1/2013 | Zemlok et al. |
| 8,365,976 B2 | 2/2013 | Hess et al. |
| 8,371,491 B2 | 2/2013 | Huitema et al. |
| 8,393,514 B2 | 3/2013 | Shelton, IV et al. |
| 8,397,971 B2 | 3/2013 | Yates et al. |
| 8,408,439 B2 | 4/2013 | Huang et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,740 B2 | 4/2013 | Shelton, IV et al. |
| 8,444,036 B2 | 5/2013 | Shelton, IV et al. |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,454,640 B2 | 6/2013 | Johnston et al. |
| 8,459,520 B2 | 6/2013 | Giordano et al. |
| 8,464,923 B2 | 6/2013 | Shelton, IV |
| 8,474,677 B2 | 7/2013 | Woodard, Jr. et al. |
| 8,479,969 B2 | 7/2013 | Shelton, IV et al. |
| 8,485,412 B2 | 7/2013 | Shelton, IV et al. |
| 8,485,413 B2 | 7/2013 | Scheib et al. |
| 8,517,239 B2 | 8/2013 | Scheib et al. |
| 8,517,243 B2 | 8/2013 | Giordano et al. |
| 8,529,600 B2 | 9/2013 | Woodard, Jr. et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,465 B2 | 11/2013 | Shelton, IV |
| 8,579,176 B2 | 11/2013 | Smith et al. |
| 8,584,919 B2 | 11/2013 | Hueil et al. |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,668,130 B2 | 3/2014 | Hess et al. |
| 8,672,207 B2 | 3/2014 | Shelton, IV et al. |
| 8,672,208 B2 | 3/2014 | Hess et al. |
| 8,672,951 B2 | 3/2014 | Smith et al. |
| 8,679,154 B2 | 3/2014 | Smith et al. |
| 8,679,156 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,733,613 B2 | 5/2014 | Huitema et al. |
| 8,734,478 B2 | 5/2014 | Widenhouse et al. |
| 2001/0029384 A1 | 10/2001 | Nicholas et al. |
| 2002/0050769 A1* | 5/2002 | Pelrine et al. ............... 310/363 |
| 2002/0074005 A1 | 6/2002 | Hogg et al. |
| 2002/0108112 A1 | 8/2002 | Wallace et al. |
| 2002/0165541 A1 | 11/2002 | Whitman |

(56) References Cited

U.S. PATENT DOCUMENTS

| | | |
|---|---|---|
| 2003/0065358 A1 | 4/2003 | Frecker et al. |
| 2003/0069474 A1 | 4/2003 | Couvillion et al. |
| 2003/0199870 A1 | 10/2003 | Truckai et al. |
| 2003/0207606 A1 | 11/2003 | Ho |
| 2004/0002726 A1 | 1/2004 | Nunez et al. |
| 2004/0054322 A1 | 3/2004 | Vargas |
| 2004/0068224 A1* | 4/2004 | Couvillon et al. .............. 604/67 |
| 2004/0097971 A1 | 5/2004 | Hughett |
| 2004/0138700 A1 | 7/2004 | Cooper et al. |
| 2004/0149802 A1 | 8/2004 | Whitman |
| 2004/0167572 A1 | 8/2004 | Roth et al. |
| 2004/0222268 A1 | 11/2004 | Bilotti et al. |
| 2004/0232195 A1 | 11/2004 | Shelton, IV et al. |
| 2004/0232196 A1 | 11/2004 | Shelton et al. |
| 2004/0232197 A1 | 11/2004 | Shelton et al. |
| 2004/0267310 A1 | 12/2004 | Racenet et al. |
| 2005/0006429 A1 | 1/2005 | Wales et al. |
| 2005/0006431 A1 | 1/2005 | Shelton, IV et al. |
| 2005/0006434 A1 | 1/2005 | Wales et al. |
| 2005/0059997 A1 | 3/2005 | Bauman et al. |
| 2005/0067457 A1 | 3/2005 | Shelton et al. |
| 2005/0067458 A1 | 3/2005 | Swayze et al. |
| 2005/0085693 A1 | 4/2005 | Belson et al. |
| 2005/0102017 A1 | 5/2005 | Mattison |
| 2005/0103819 A1 | 5/2005 | Racenet et al. |
| 2005/0131436 A1 | 6/2005 | Johnston et al. |
| 2005/0131457 A1 | 6/2005 | Douglas et al. |
| 2005/0165415 A1 | 7/2005 | Wales |
| 2005/0173490 A1 | 8/2005 | Shelton |
| 2005/0177181 A1 | 8/2005 | Kagan et al. |
| 2005/0184121 A1* | 8/2005 | Heinrich .................. 227/175.1 |
| 2005/0216055 A1 | 9/2005 | Scirica et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0041273 A1 | 2/2006 | Ortiz et al. |
| 2006/0047302 A1 | 3/2006 | Ortiz et al. |
| 2006/0047303 A1 | 3/2006 | Ortiz et al. |
| 2006/0047305 A1 | 3/2006 | Ortiz et al. |
| 2006/0047306 A1 | 3/2006 | Ortiz et al. |
| 2006/0047307 A1 | 3/2006 | Ortiz et al. |
| 2006/0047308 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0180634 A1 | 8/2006 | Shelton, IV et al. |
| 2006/0190028 A1 | 8/2006 | Wales et al. |
| 2006/0212069 A1 | 9/2006 | Shelton, IV et al. |
| 2006/0241692 A1 | 10/2006 | McGuckin, Jr. et al. |
| 2006/0259073 A1 | 11/2006 | Miyamoto et al. |
| 2006/0271102 A1 | 11/2006 | Bosshard et al. |
| 2006/0289602 A1 | 12/2006 | Wales et al. |
| 2007/0027468 A1 | 2/2007 | Wales et al. |
| 2007/0073341 A1 | 3/2007 | Smith et al. |
| 2007/0078484 A1 | 4/2007 | Talarico et al. |
| 2007/0084897 A1 | 4/2007 | Shelton, IV et al. |
| 2007/0102453 A1 | 5/2007 | Morgan et al. |
| 2007/0102472 A1 | 5/2007 | Shelton IV |
| 2007/0106317 A1 | 5/2007 | Shelton IV et al. |
| 2007/0170225 A1 | 7/2007 | Shelton IV et al. |
| 2007/0175950 A1 | 8/2007 | Shelton IV et al. |
| 2007/0175951 A1 | 8/2007 | Shelton IV et al. |
| 2007/0175955 A1 | 8/2007 | Shelton IV et al. |
| 2007/0179525 A1 | 8/2007 | Frecker et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2008/0015598 A1 | 1/2008 | Prommersberger |
| 2008/0029570 A1 | 2/2008 | Shelton IV et al. |
| 2008/0029573 A1 | 2/2008 | Shelton IV et al. |
| 2008/0029574 A1 | 2/2008 | Shelton IV et al. |
| 2008/0029575 A1 | 2/2008 | Shelton IV et al. |
| 2008/0078802 A1 | 4/2008 | Hess et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0169328 A1 | 7/2008 | Shelton IV et al. |
| 2008/0169331 A1 | 7/2008 | Shelton IV et al. |
| 2008/0169332 A1 | 7/2008 | Shelton IV et al. |
| 2008/0169333 A1 | 7/2008 | Shelton IV et al. |
| 2008/0296346 A1 | 12/2008 | Shelton, IV et al. |
| 2008/0308602 A1 | 12/2008 | Timm et al. |
| 2008/0308603 A1 | 12/2008 | Shelton IV et al. |
| 2009/0001121 A1 | 1/2009 | Hess et al. |
| 2009/0001130 A1 | 1/2009 | Hess et al. |
| 2009/0005807 A1 | 1/2009 | Hess et al. |
| 2009/0005809 A1 | 1/2009 | Hess et al. |
| 2009/0012556 A1 | 1/2009 | Boudreaux et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0242610 A1 | 10/2009 | Shelton, IV et al. |
| 2010/0069942 A1 | 3/2010 | Shelton, IV et al. |
| 2010/0076475 A1 | 3/2010 | Yates et al. |
| 2010/0133317 A1 | 6/2010 | Shelton, IV et al. |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0222901 A1 | 9/2010 | Swayze et al. |
| 2010/0258611 A1 | 10/2010 | Smith et al. |
| 2010/0294829 A1 | 11/2010 | Giordano et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall et al. |
| 2011/0024478 A1 | 2/2011 | Shelton, IV et al. |
| 2011/0060363 A1 | 3/2011 | Hess et al. |
| 2011/0068148 A1 | 3/2011 | Hall et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0114700 A1 | 5/2011 | Baxter, III et al. |
| 2011/0125176 A1 | 5/2011 | Yates et al. |
| 2011/0125177 A1 | 5/2011 | Yates et al. |
| 2011/0132964 A1 | 6/2011 | Weisenburgh, II et al. |
| 2011/0144430 A1 | 6/2011 | Spivey et al. |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295295 A1 | 12/2011 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |

(56) References Cited

U.S. PATENT DOCUMENTS

| | | |
|---|---|---|
| 2012/0029547 A1 | 2/2012 | Shelton, IV et al. |
| 2012/0071711 A1 | 3/2012 | Shelton, IV et al. |
| 2012/0074196 A1 | 3/2012 | Shelton, IV et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080478 A1 | 4/2012 | Morgan et al. |
| 2012/0080479 A1 | 4/2012 | Shelton, IV et al. |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton, IV et al. |
| 2012/0199630 A1 | 8/2012 | Shelton, IV et al. |
| 2012/0199632 A1 | 8/2012 | Spivey et al. |
| 2012/0203247 A1 | 8/2012 | Shelton, IV et al. |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0283707 A1 | 11/2012 | Giordano et al. |
| 2012/0292367 A1 | 11/2012 | Morgan et al. |
| 2012/0298719 A1 | 11/2012 | Shelton, IV et al. |

FOREIGN PATENT DOCUMENTS

| | | |
|---|---|---|
| CA | 2512960 | 1/2006 |
| CA | 2514274 | 1/2006 |
| CN | 1634601 | 7/2005 |
| CN | 1868411 | 11/2006 |
| CN | 1915180 | 2/2007 |
| CN | 101095621 | 1/2008 |
| DE | 273689 | 5/1914 |
| DE | 1993372 | 9/1968 |
| DE | 1775926 | 1/1972 |
| DE | 3036217 | 4/1982 |
| DE | 3210466 | 9/1983 |
| DE | 4015562 | 11/1991 |
| DE | 4303544 | 9/1993 |
| DE | 9412228 | 9/1994 |
| DE | 19509116 | 9/1996 |
| DE | 19534320 | 2/1997 |
| DE | 19537299 | 4/1997 |
| DE | 19643073 | 4/1997 |
| DE | 19647354 | 5/1998 |
| DE | 19851291 | 1/2000 |
| DE | 19924311 | 11/2000 |
| DE | 69328576 | 1/2001 |
| DE | 10052679 | 5/2001 |
| DE | 20112837 | 10/2001 |
| DE | 20121753 | 4/2003 |
| DE | 10314072 | 10/2004 |
| DE | 202007003114 | 6/2007 |
| EP | 0122046 | 10/1984 |
| EP | 0070230 | 10/1985 |
| EP | 0387980 | 10/1985 |
| EP | 0033548 | 5/1986 |
| EP | 0 201 883 | 11/1986 |
| EP | 0276104 | 7/1988 |
| EP | 0 500 353 | 8/1992 |
| EP | 0248844 | 1/1993 |
| EP | 0545029 | 6/1993 |
| EP | 0277959 | 10/1993 |
| EP | 0233940 | 11/1993 |
| EP | 0261230 | 11/1993 |
| EP | 0639349 | 2/1994 |
| EP | 0324636 | 3/1994 |
| EP | 0593920 | 4/1994 |
| EP | 0594148 | 4/1994 |
| EP | 0427949 | 6/1994 |
| EP | 0523174 | 6/1994 |
| EP | 0600182 | 6/1994 |
| EP | 0310431 | 11/1994 |
| EP | 0375302 | 11/1994 |
| EP | 0376562 | 11/1994 |
| EP | 0630612 | 12/1994 |
| EP | 0634144 | 1/1995 |
| EP | 0646356 | 4/1995 |
| EP | 0646357 | 4/1995 |
| EP | 0653189 | 5/1995 |
| EP | 0669104 | 8/1995 |
| EP | 0 674 876 | 10/1995 |
| EP | 0511470 | 10/1995 |
| EP | 0679367 | 11/1995 |
| EP | 0392547 | 12/1995 |
| EP | 0685204 | 12/1995 |
| EP | 0364216 | 1/1996 |
| EP | 0699418 | 3/1996 |
| EP | 0702937 | 3/1996 |
| EP | 0705571 | 4/1996 |
| EP | 0711611 | 5/1996 |
| EP | 0484677 | 6/1996 |
| EP | 0541987 | 7/1996 |
| EP | 0667119 | 7/1996 |
| EP | 0 741 996 | 11/1996 |
| EP | 0741966 | 11/1996 |
| EP | 0708618 | 3/1997 |
| EP | 0770355 | 5/1997 |
| EP | 0503662 | 6/1997 |

(56) References Cited

FOREIGN PATENT DOCUMENTS

| | | |
|---|---|---|
| EP | 0447121 | 7/1997 |
| EP | 0625077 | 7/1997 |
| EP | 0633749 | 8/1997 |
| EP | 0710090 | 8/1997 |
| EP | 0578425 | 9/1997 |
| EP | 0625335 | 11/1997 |
| EP | 0552423 | 1/1998 |
| EP | 0592244 | 1/1998 |
| EP | 0648476 | 1/1998 |
| EP | 0649290 | 3/1998 |
| EP | 0829235 | 3/1998 |
| EP | 0 832 605 | 4/1998 |
| EP | 0598618 | 9/1998 |
| EP | 0676173 | 9/1998 |
| EP | 0678007 | 9/1998 |
| EP | 0603472 | 11/1998 |
| EP | 0605351 | 11/1998 |
| EP | 0878169 | 11/1998 |
| EP | 0879742 | 11/1998 |
| EP | 0695144 | 12/1998 |
| EP | 0722296 | 12/1998 |
| EP | 0760230 | 2/1999 |
| EP | 0623316 | 3/1999 |
| EP | 0650701 | 3/1999 |
| EP | 0537572 | 6/1999 |
| EP | 0923907 | 6/1999 |
| EP | 0843906 | 3/2000 |
| EP | 0552050 | 5/2000 |
| EP | 0833592 | 5/2000 |
| EP | 0830094 | 9/2000 |
| EP | 1034747 | 9/2000 |
| EP | 1034748 | 9/2000 |
| EP | 0694290 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1090592 | 4/2001 |
| EP | 1095627 | 5/2001 |
| EP | 1256318 | 5/2001 |
| EP | 0806914 | 9/2001 |
| EP | 0768840 | 12/2001 |
| EP | 0908152 | 1/2002 |
| EP | 0872213 | 5/2002 |
| EP | 0862386 | 6/2002 |
| EP | 0949886 | 9/2002 |
| EP | 1238634 | 9/2002 |
| EP | 0858295 | 12/2002 |
| EP | 0656188 | 1/2003 |
| EP | 1284120 | 2/2003 |
| EP | 1287788 | 3/2003 |
| EP | 0717966 | 4/2003 |
| EP | 0869742 | 5/2003 |
| EP | 0887046 | 7/2003 |
| EP | 1323384 | 7/2003 |
| EP | 0852480 | 8/2003 |
| EP | 0891154 | 9/2003 |
| EP | 0813843 | 10/2003 |
| EP | 0873089 | 10/2003 |
| EP | 0856326 | 11/2003 |
| EP | 1374788 | 1/2004 |
| EP | 0814712 | 2/2004 |
| EP | 1402837 | 3/2004 |
| EP | 0705570 | 4/2004 |
| EP | 0959784 | 4/2004 |
| EP | 1407719 | 4/2004 |
| EP | 1086713 | 5/2004 |
| EP | 0996378 | 6/2004 |
| EP | 1426012 | 6/2004 |
| EP | 0833593 | 7/2004 |
| EP | 1442694 | 8/2004 |
| EP | 0888749 | 9/2004 |
| EP | 0959786 | 9/2004 |
| EP | 1459695 | 9/2004 |
| EP | 1473819 | 11/2004 |
| EP | 1477119 | 11/2004 |
| EP | 1479345 | 11/2004 |
| EP | 1479347 | 11/2004 |
| EP | 1479348 | 11/2004 |
| EP | 0754437 | 12/2004 |
| EP | 1025807 | 12/2004 |
| EP | 1001710 | 1/2005 |
| EP | 1 522 264 | 4/2005 |
| EP | 1520521 | 4/2005 |
| EP | 1520523 | 4/2005 |
| EP | 1520525 | 4/2005 |
| EP | 1523942 | 4/2005 |
| EP | 1550408 | 7/2005 |
| EP | 1557129 | 7/2005 |
| EP | 1064883 | 8/2005 |
| EP | 1067876 | 8/2005 |
| EP | 0870473 | 9/2005 |
| EP | 1157666 | 9/2005 |
| EP | 0880338 | 10/2005 |
| EP | 1158917 | 11/2005 |
| EP | 1344498 | 11/2005 |
| EP | 1330989 | 12/2005 |
| EP | 0771176 | 1/2006 |
| EP | 1621137 | 2/2006 |
| EP | 1621138 | 2/2006 |
| EP | 1621139 | 2/2006 |
| EP | 1621141 | 2/2006 |
| EP | 1621143 | 2/2006 |
| EP | 1621145 | 2/2006 |
| EP | 1621151 | 2/2006 |
| EP | 1034746 | 3/2006 |
| EP | 1632191 | 3/2006 |
| EP | 1065981 | 5/2006 |
| EP | 1082944 | 5/2006 |
| EP | 1652481 | 5/2006 |
| EP | 1382303 | 6/2006 |
| EP | 1253866 | 7/2006 |
| EP | 1032318 | 8/2006 |
| EP | 1045672 | 8/2006 |
| EP | 1617768 | 8/2006 |
| EP | 1693008 | 8/2006 |
| EP | 1693015 | 8/2006 |
| EP | 1400214 | 9/2006 |
| EP | 1702567 | 9/2006 |
| EP | 1129665 | 11/2006 |
| EP | 1400206 | 11/2006 |
| EP | 1721568 | 11/2006 |
| EP | 1256317 | 12/2006 |
| EP | 1285633 | 12/2006 |
| EP | 1728473 | 12/2006 |
| EP | 1728475 | 12/2006 |
| EP | 1479346 | 1/2007 |
| EP | 1484024 | 1/2007 |
| EP | 1754445 | 2/2007 |
| EP | 1759812 | 3/2007 |
| EP | 1767163 | 3/2007 |
| EP | 1769756 | 4/2007 |
| EP | 1769758 | 4/2007 |
| EP | 1581128 | 5/2007 |
| EP | 1785097 | 5/2007 |
| EP | 1790293 | 5/2007 |
| EP | 1800610 | 6/2007 |
| EP | 1300117 | 8/2007 |
| EP | 1813199 | 8/2007 |
| EP | 1813201 | 8/2007 |
| EP | 1813203 | 8/2007 |
| EP | 1813207 | 8/2007 |
| EP | 1813209 | 8/2007 |
| EP | 1487359 | 10/2007 |
| EP | 1599146 | 10/2007 |
| EP | 1839596 | 10/2007 |
| EP | 2110083 | 10/2007 |
| EP | 1857057 | 11/2007 |
| EP | 1402821 | 12/2007 |
| EP | 1872727 | 1/2008 |
| EP | 1897502 | 3/2008 |
| EP | 1330201 | 6/2008 |

(56) References Cited

FOREIGN PATENT DOCUMENTS

| | | |
|---|---|---|
| EP | 1702568 | 7/2008 |
| EP | 1943957 | 7/2008 |
| EP | 1943964 | 7/2008 |
| EP | 1943976 | 7/2008 |
| EP | 1593337 | 8/2008 |
| EP | 1970014 | 9/2008 |
| EP | 1980213 | 10/2008 |
| EP | 1759645 | 11/2008 |
| EP | 1990014 | 11/2008 |
| EP | 1759640 | 12/2008 |
| EP | 2000102 | 12/2008 |
| EP | 2008595 | 12/2008 |
| EP | 1736104 | 3/2009 |
| EP | 1749486 | 3/2009 |
| EP | 2039316 | 3/2009 |
| EP | 1721576 | 4/2009 |
| EP | 1733686 | 4/2009 |
| EP | 2044890 | 4/2009 |
| EP | 1550413 | 6/2009 |
| EP | 1745748 | 8/2009 |
| EP | 2090237 | 8/2009 |
| EP | 2090256 | 8/2009 |
| EP | 2095777 | 9/2009 |
| EP | 2110082 | 10/2009 |
| EP | 1813208 | 11/2009 |
| EP | 2116195 | 11/2009 |
| EP | 1607050 | 12/2009 |
| EP | 1815804 | 12/2009 |
| EP | 1566150 | 4/2010 |
| EP | 1813206 | 4/2010 |
| EP | 1769754 | 6/2010 |
| EP | 1990014 | 6/2010 |
| EP | 1535565 | 10/2010 |
| EP | 1702570 | 10/2010 |
| EP | 1785098 | 10/2010 |
| EP | 2030578 | 11/2010 |
| EP | 1627605 | 12/2010 |
| EP | 1813205 | 6/2011 |
| EP | 1785102 | 1/2012 |
| FR | 999646 | 2/1952 |
| FR | 1112936 | 3/1956 |
| FR | 2598905 | 11/1987 |
| FR | 2765794 | 1/1999 |
| GB | 939929 | 10/1963 |
| GB | 1210522 | 10/1970 |
| GB | 1217159 | 12/1970 |
| GB | 1339394 | 12/1973 |
| GB | 2109241 | 6/1983 |
| GB | 2272159 | 5/1994 |
| GB | 2284242 | 5/1995 |
| GB | 2336214 | 10/1999 |
| GB | 2425903 | 11/2006 |
| JP | 58500053 | 1/1983 |
| JP | 61-98249 | 5/1986 |
| JP | 63-203149 | 8/1988 |
| JP | 3-12126 | 1/1991 |
| JP | 5-212039 | 8/1993 |
| JP | 6-007357 | 1/1994 |
| JP | 6-189969 | 7/1994 |
| JP | 07-47070 | 2/1995 |
| JP | 07-51273 | 2/1995 |
| JP | 08-33641 | 2/1996 |
| JP | 08-229050 | 9/1996 |
| JP | 08-336540 | 12/1996 |
| JP | 08-336544 | 12/1996 |
| JP | 10-113352 | 5/1998 |
| JP | 2000-033071 | 2/2000 |
| JP | 2000-171730 | 6/2000 |
| JP | 2000-287987 | 10/2000 |
| JP | 2000-325303 | 11/2000 |
| JP | 2001-514571 | 9/2001 |
| JP | 2001-517473 | 10/2001 |
| JP | 2001286477 | 10/2001 |
| JP | 2002143078 | 5/2002 |
| JP | 2002-204801 | 7/2002 |
| JP | 2002-314298 | 10/2002 |
| JP | 2002369820 | 12/2002 |
| JP | 2003-523254 | 8/2003 |
| JP | 2004-136112 | 5/2004 |
| JP | 2004344663 | 12/2004 |
| JP | 2005028149 | 2/2005 |
| JP | 2005505322 | 2/2005 |
| JP | 2005-80702 | 3/2005 |
| JP | 2005103293 | 4/2005 |
| JP | 2005131163 | 5/2005 |
| JP | 2005131164 | 5/2005 |
| JP | 2005131173 | 5/2005 |
| JP | 2005131211 | 5/2005 |
| JP | 2005131212 | 5/2005 |
| JP | 2005137423 | 6/2005 |
| JP | 2005152416 | 6/2005 |
| JP | 2005523105 | 8/2005 |
| JP | 2005524474 | 8/2005 |
| JP | 2006281405 | 10/2006 |
| JP | 2004-162035 | 6/2010 |
| RU | 2008830 | 3/1994 |
| RU | 2187249 | 8/2002 |
| RU | 2225170 | 3/2004 |
| SU | 189517 | 1/1967 |
| SU | 328636 | 9/1972 |
| SU | 886900 | 12/1981 |
| SU | 1009439 | 4/1983 |
| SU | 1333319 | 8/1987 |
| SU | 1377053 | 2/1988 |
| SU | 1561964 | 5/1990 |
| SU | 1722476 | 3/1992 |
| WO | WO 82/02824 | 9/1982 |
| WO | WO 91/15157 | 10/1991 |
| WO | WO 92/20295 | 11/1992 |
| WO | WO 92/21300 | 12/1992 |
| WO | WO 93/08755 | 5/1993 |
| WO | WO 93/13718 | 7/1993 |
| WO | WO 93/14690 | 8/1993 |
| WO | WO 93/15648 | 8/1993 |
| WO | WO 93/15850 | 8/1993 |
| WO | WO 93/19681 | 10/1993 |
| WO | WO 94/00060 | 1/1994 |
| WO | WO 94/11057 | 5/1994 |
| WO | WO 94/12108 | 6/1994 |
| WO | WO 94/18893 | 9/1994 |
| WO | WO 94/22378 | 10/1994 |
| WO | WO 94/23659 | 10/1994 |
| WO | WO 95/02369 | 1/1995 |
| WO | WO 95/03743 | 2/1995 |
| WO | WO 95/06817 | 3/1995 |
| WO | WO 95/09576 | 4/1995 |
| WO | WO 95/09577 | 4/1995 |
| WO | WO 95/14436 | 6/1995 |
| WO | WO 95/17855 | 7/1995 |
| WO | WO 95/18383 | 7/1995 |
| WO | WO 95/18572 | 7/1995 |
| WO | WO 95/19739 | 7/1995 |
| WO | WO 95/20360 | 8/1995 |
| WO | WO 95/23557 | 9/1995 |
| WO | WO 95/24865 | 9/1995 |
| WO | WO 95/25471 | 9/1995 |
| WO | WO 95/26562 | 10/1995 |
| WO | WO 95/29639 | 11/1995 |
| WO | WO 96/04858 | 2/1996 |
| WO | WO 96/19151 | 6/1996 |
| WO | WO 96/19152 | 6/1996 |
| WO | WO 96/20652 | 7/1996 |
| WO | WO 96/21119 | 7/1996 |
| WO | WO 96/22055 | 7/1996 |
| WO | WO 96/23448 | 8/1996 |
| WO | WO 96/24301 | 8/1996 |
| WO | WO 96/27337 | 9/1996 |
| WO | WO 96/31155 | 10/1996 |
| WO | WO 96/35464 | 11/1996 |
| WO | WO 96/39085 | 12/1996 |
| WO | WO 96/39086 | 12/1996 |
| WO | WO 96/39087 | 12/1996 |
| WO | WO 96/39088 | 12/1996 |
| WO | WO 96/39089 | 12/1996 |

(56) References Cited

FOREIGN PATENT DOCUMENTS

| | | |
|---|---|---|
| WO | WO 97/00646 | 1/1997 |
| WO | WO 97/00647 | 1/1997 |
| WO | WO 97/06582 | 2/1997 |
| WO | WO 97/10763 | 3/1997 |
| WO | WO 97/10764 | 3/1997 |
| WO | WO 97/11648 | 4/1997 |
| WO | WO 97/11649 | 4/1997 |
| WO | WO 97/15237 | 5/1997 |
| WO | WO 97/24073 | 7/1997 |
| WO | WO 97/24993 | 7/1997 |
| WO | WO 97/30644 | 8/1997 |
| WO | WO 97/34533 | 9/1997 |
| WO | WO 97/37598 | 10/1997 |
| WO | WO 97/39688 | 10/1997 |
| WO | WO 98/17180 | 4/1998 |
| WO | WO 98/27880 | 7/1998 |
| WO | WO 98/30153 | 7/1998 |
| WO | WO 98/47436 | 10/1998 |
| WO | WO 99/02090 | 1/1999 |
| WO | WO 99/03407 | 1/1999 |
| WO | WO 99/03408 | 1/1999 |
| WO | WO 99/03409 | 1/1999 |
| WO | WO 99/12483 | 3/1999 |
| WO | WO 99/12487 | 3/1999 |
| WO | WO 99/12488 | 3/1999 |
| WO | WO 99/15086 | 4/1999 |
| WO | WO 99/15091 | 4/1999 |
| WO | WO 99/23933 | 5/1999 |
| WO | WO 99/23959 | 5/1999 |
| WO | WO 99/25261 | 5/1999 |
| WO | WO 99/29244 | 6/1999 |
| WO | WO 99/34744 | 7/1999 |
| WO | WO 99/45849 | 9/1999 |
| WO | WO 99/48430 | 9/1999 |
| WO | WO 99/51158 | 10/1999 |
| WO | WO 00/24322 | 5/2000 |
| WO | WO 00/24330 | 5/2000 |
| WO | WO 00/41638 | 7/2000 |
| WO | WO 00/48506 | 8/2000 |
| WO | WO 00/53112 | 9/2000 |
| WO | WO 00/54653 | 9/2000 |
| WO | WO 00/57796 | 10/2000 |
| WO | WO 00/64365 | 11/2000 |
| WO | WO 00/72762 | 12/2000 |
| WO | WO 00/72765 | 12/2000 |
| WO | WO 00/78222 | 12/2000 |
| WO | WO 01/03587 | 1/2001 |
| WO | WO 01/05702 | 1/2001 |
| WO | WO 01/10482 | 2/2001 |
| WO | WO 01/35845 | 5/2001 |
| WO | WO 01/54594 | 8/2001 |
| WO | WO 01/56455 | 8/2001 |
| WO | WO 01/58371 | 8/2001 |
| WO | WO 01/62158 | 8/2001 |
| WO | WO 01/62161 | 8/2001 |
| WO | WO 01/62162 | 8/2001 |
| WO | WO 01/62163 | 8/2001 |
| WO | WO 01/62164 | 8/2001 |
| WO | WO 01/62169 | 8/2001 |
| WO | WO 01/78605 | 10/2001 |
| WO | WO 01/91646 | 12/2001 |
| WO | WO 02/07608 | 1/2002 |
| WO | WO 02/07618 | 1/2002 |
| WO | WO 02/17799 | 3/2002 |
| WO | WO 02/19920 | 3/2002 |
| WO | WO 02/19932 | 3/2002 |
| WO | WO 02/28268 | 4/2002 |
| WO | WO 02/30297 | 4/2002 |
| WO | WO 02/32322 | 4/2002 |
| WO | WO 02/36028 | 5/2002 |
| WO | WO 02/43571 | 6/2002 |
| WO | WO 02/058568 | 8/2002 |
| WO | WO 02/060328 | 8/2002 |
| WO | WO 02/067785 | 9/2002 |
| WO | WO 02/098302 | 12/2002 |
| WO | WO 03/000138 | 1/2003 |
| WO | WO 03/001329 | 1/2003 |
| WO | WO 03/013363 | 2/2003 |
| WO | WO 03/015604 | 2/2003 |
| WO | WO 03/020106 | 3/2003 |
| WO | WO 03/020139 | 3/2003 |
| WO | WO 03/024339 | 3/2003 |
| WO | WO 03/079909 | 3/2003 |
| WO | WO 03/030743 | 4/2003 |
| WO | WO 03/037193 | 5/2003 |
| WO | WO 03/047436 | 6/2003 |
| WO | WO 03/055402 | 7/2003 |
| WO | WO 03/057048 | 7/2003 |
| WO | WO 03/057058 | 7/2003 |
| WO | WO 03/063694 | 8/2003 |
| WO | WO 03/077769 | 9/2003 |
| WO | WO 03/079911 | 10/2003 |
| WO | WO 03/082126 | 10/2003 |
| WO | WO 03/088845 | 10/2003 |
| WO | WO 03/090630 | 11/2003 |
| WO | WO 03/094743 | 11/2003 |
| WO | WO 03/094745 | 11/2003 |
| WO | WO 03/094746 | 11/2003 |
| WO | WO 03/094747 | 11/2003 |
| WO | WO 03/101313 | 12/2003 |
| WO | WO 03/105698 | 12/2003 |
| WO | WO 03/105702 | 12/2003 |
| WO | WO 2004/006980 | 1/2004 |
| WO | WO 2004/011037 | 2/2004 |
| WO | WO 2004/014238 | 2/2004 |
| WO | WO 2004/019769 | 3/2004 |
| WO | WO 2004/021868 | 3/2004 |
| WO | WO 2004/028585 | 4/2004 |
| WO | WO 2004/032754 | 4/2004 |
| WO | WO 2004/032760 | 4/2004 |
| WO | WO 2004/032762 | 4/2004 |
| WO | WO 2004/032763 | 4/2004 |
| WO | WO 2004/034875 | 4/2004 |
| WO | WO 2004/047626 | 6/2004 |
| WO | WO 2004/047653 | 6/2004 |
| WO | WO 2004/049956 | 6/2004 |
| WO | WO 2004/050971 | 6/2004 |
| WO | WO 2004/052426 | 6/2004 |
| WO | WO 2004/056276 | 7/2004 |
| WO | WO 2004/056277 | 7/2004 |
| WO | WO 2004/062516 | 7/2004 |
| WO | WO 2004/078050 | 9/2004 |
| WO | WO 2004/078051 | 9/2004 |
| WO | WO 2004/086987 | 10/2004 |
| WO | WO 2004/096015 | 11/2004 |
| WO | WO 2004/096057 | 11/2004 |
| WO | WO 2004/103157 | 12/2004 |
| WO | WO 2004/105593 | 12/2004 |
| WO | WO 2004/105621 | 12/2004 |
| WO | WO 2004/112618 | 12/2004 |
| WO | WO 2004/112652 | 12/2004 |
| WO | WO 2005/027983 | 3/2005 |
| WO | WO 2005/037329 | 4/2005 |
| WO | WO 2005/044078 | 5/2005 |
| WO | WO 2005/055846 | 6/2005 |
| WO | WO 2005/072634 | 8/2005 |
| WO | WO 2005/078892 | 8/2005 |
| WO | WO 2005/079675 | 9/2005 |
| WO | WO 2005/096954 | 10/2005 |
| WO | WO 2005/112806 | 12/2005 |
| WO | WO 2005/112808 | 12/2005 |
| WO | WO 2005/115251 | 12/2005 |
| WO | WO 2005/115253 | 12/2005 |
| WO | WO 2005/117735 | 12/2005 |
| WO | WO 2005/122936 | 12/2005 |
| WO | WO 2006/027014 | 3/2006 |
| WO | WO 2006/044490 | 4/2006 |
| WO | WO 2006/044581 | 4/2006 |
| WO | WO 2006/044810 | 4/2006 |
| WO | WO 2006/051252 | 5/2006 |
| WO | WO 2006/059067 | 6/2006 |
| WO | WO 2006/083748 | 8/2006 |
| WO | WO 2006/092563 | 9/2006 |
| WO | WO 2006/092565 | 9/2006 |

(56) References Cited

FOREIGN PATENT DOCUMENTS

| WO | WO 2006/115958 | 11/2006 |
|---|---|---|
| WO | WO 2006/132992 | 12/2006 |
| WO | WO 2007/002180 | 1/2007 |
| WO | WO 2007/016290 | 2/2007 |
| WO | WO 2007/018898 | 2/2007 |
| WO | WO 2007/098220 | 8/2007 |
| WO | WO 2007/121579 | 11/2007 |
| WO | WO 2007/131110 | 11/2007 |
| WO | WO 2007/137304 | 11/2007 |
| WO | WO 2007/139734 | 12/2007 |
| WO | WO 2007/142625 | 12/2007 |
| WO | WO 2007/147439 | 12/2007 |
| WO | WO 2008/021969 | 2/2008 |
| WO | WO 2008/039249 | 4/2008 |
| WO | WO 2008/039270 | 4/2008 |
| WO | WO 2008/045383 | 4/2008 |
| WO | WO 2008/070763 | 6/2008 |
| WO | WO 2008/089404 | 7/2008 |
| WO | WO 2008/109125 | 9/2008 |
| WO | WO 2006/125940 | 11/2009 |
| WO | WO 2010/063795 | 6/2010 |
| WO | WO 2012/044844 | 4/2012 |

OTHER PUBLICATIONS

European Search Report dated Mar. 27, 2008 for Application 05254684.
Non-Final Rejection dated Nov. 13, 2006 for U.S. Appl. No. 11/181,046.
Non-Final Rejection dated Aug. 7, 2007 for U.S. Appl. No. 11/162,990.
Non-Final Rejection dated Aug. 29, 2007 for U.S. Appl. No. 11/181,046.
Non-Final Rejection dated Sep. 21, 2007 for U.S. Appl. No. 11/162,986.
Non-Final Rejection dated Sep. 21, 2007 for U.S. Appl. No. 11/162,988.
Notice of Allowance dated May 23, 2006 for U.S. Appl. No. 11/096,158.
Notice of Allowance dated Jul. 25, 2006 for U.S. Appl. No. 11/066,371.
Notice of Allowance dated Aug. 14, 2006 for U.S. Appl. No. 11/157,767.
Notice of Allowance dated Aug. 22, 2006 for U.S. Appl. No. 11/181,471.
Notice of Allowance dated Sep. 25, 2006 for U.S. Appl. No. 11/083,470.
Notice of Allowance dated Dec. 1, 2006 for U.S. Appl. No. 10/955,042.
Notice of Allowance dated Aug. 31, 2007 for U.S. Appl. No. 11/096,096.
Notice of Allowance dated Sep. 12, 2007 for U.S. Appl. No. 11/140,836.
Notice of Allowance dated Sep. 19, 2007 for U.S. Appl. No. 11/082,495.
Notice of Allowance dated Oct. 1, 2007 for U.S. Appl. No. 10/955,042.
Notice of Allowance dated Mar. 13, 2008 for U.S. Appl. No. 11/240,836.
U.S. Appl. No. 10/441,362, filed May 20, 2003, Ho.
U.S. Appl. No. 60/591,694, filed Jul. 28, 2004, Shelton IV.
Office Action dated Mar. 15, 2006 for U.S. Appl. No. 10/955,042.
Office Action dated Mar. 22, 2007 for U.S. Appl. No. 11/082,495.
Office Action dated Mar. 29, 2007 for U.S. Appl. No. 10/955,042.
Examination Report for Application 05254680, Sep. 22, 2006.
Examination Report for Application 05254685, Sep. 22, 2006.
Examination Report for Application 05254694, Sep. 22, 2006.
Examination Report for Application 05254695, Sep. 22, 2006.
Notice of Allowance for U.S. Appl. No. 11/083,740 dated Sep. 25, 2006.
Guidelines for Hand and Power Tools' http://www.osha.gov/doc/outreachtraining/htmlfiles/tools.html, OSHA, May 1996, page 3.
EPO Search Report, Application No. 05254680.1, Jan. 12, 2006, pp. 1-5.
EPO Search Report, Application No. 05254694.2, Jan. 12, 2006, pp. 1-5.
EPO Search Report, Application No. 05254685.0, Jan. 12, 2006, pp. 1-5.
EPO Search Report, Application No. 05254695.9, Jan. 12, 2006, pp. 1-5.
Final Rejection dated Oct. 18, 2006 for U.S. Appl. No. 11/096,096.
Non-Final Rejection dated May 5, 2008 for U.S. Appl. No. 11/181,046.
Notice of Allowance dated Jan. 5, 2007 for U.S. Appl. No. 11/096,096.
Notice of Allowance dated Mar. 25, 2008 for U.S. Appl. No. 11/096,096.
Notice of Allowance dated Apr. 10, 2008 for U.S. Appl. No. 11/082,495.
Notice of Allowance dated Apr. 10, 2008 for U.S. Appl. No. 11/162,990.
Notice of Allowance dated Apr. 18, 2008 for U.S. Appl. No. 11/162,985.
Notice of Allowance dated Apr. 18, 2008 for U.S. Appl. No. 11/162,986.
Notice of Allowance dated Apr. 18, 2008 for U.S. Appl. No. 11/162,988.
Notice of Allowance dated Jun. 10, 2008 for U.S. Appl. No. 11/082,495.
Notice of Allowance dated Jun. 10, 2008 for U.S. Appl. No. 11/240,836.
Notice of Allowance dated Aug. 11, 2008 for U.S. Appl. No. 11/082,495.
Office Action dated Mar. 15, 2008 for U.S. Appl. No. 10/955,042.
Office Action dated Mar. 22, 2008 for U.S. Appl. No. 11/082,495.
EPO Search Report dated Feb. 29, 2008 for Application No. 05254681.9.
EPO Search Report dated Mar. 3, 2008 for Application No. 05254699.1.
EPO Search Report dated Feb. 26, 2008 for Application No. 05254700.7.
EPO Search Report dated Mar. 25, 2008 for Application No. 05254703.1.
EPO Search Report dated Jan. 31, 2007 for Application No. 06255058.
EPO Search Report, Application No. 06255062.9, Nov. 23, 2006, pp. 1-3.
EPO Search Report, Application No. 06255053.8, Jan. 25, 2007, pp. 1-3.
EPO Search Report, Application No. 06255057.9, Jan. 29, 2007, pp. 1-3.
EPO Search Report, Application No. 06255064.5, Feb. 9, 2007, pp. 1-3.
EPO Search Report, Application No. 06255065.2, Feb. 15, 2007, pp. 1-3.
Japanese Interrogation/Office Action dated Jan. 15, 2013 for Application No. 2006-267300, with English Translation.
English Abstract of Japanese Publication No. JP 6-189969.
Disclosed Anonymously, "Motor-Driven Surgical Stapler Improvements," Research Disclosure Database No. 526041, Published: Feb. 2008.
Breedveld et al., "A New, Easily Miniaturized Sten-able Endoscope," IEEE Engineering in Medicidne and Biology Magazine (Nov.-Dec. 2005).
Coolman, B.R. DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet-=&journalCode=vsu which redirects to http://www3.interscience.wiley.com/journal/119040681/abstract?CRETRY=1&SR-ETRY=0; [online] accessed: Sep. 22, 2008 (2 pages).

(56) References Cited

OTHER PUBLICATIONS

Thompson, C.C. et al., "Peroral Endoscopic Reduction of Dilated Gastrojejunal Anastomosis After Roux-en-Y Gastic Bypass: A Possible New Option for Patients with Weight Regain," Surg Endose (2006) vol. 20, pp. 1744-1748.
Tuite, D. ED, "Get the Lowdown on Ultracapacitors," Nov. 15, 2007; [online] URL: http://electronicdesign.com/Articles/Print.cfm?ArticleID=17465, accessed Jan. 15, 2008 (5 pages).
Van Meer et al., "A Disposable Plastic Compact Wrist for Smart Minimally Invasive Surgical Tools," LAAS/CNRS (Aug. 2005).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Datasheet for Panasonic TK Relays Ultra Low Profile 2 A Polarized Relay, Copyright Matsushita Electric Works, Ltd. (Known of at least as early as Aug. 17, 2010).
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Australian Office Action, Examiner's First Report, dated May 24, 2010 for Application No. AU 2005203212.
Australian Office Action, Examiner's First Report, dated May 24, 2010 for Application No. AU 2005203213.
Australian Office Action, Examiner's First Report, dated May 24, 2010 for Application No. AU 2005203217.
Australian Office Action, Examiner's First Report, dated May 12, 2010 for Application No. AU 2005203222.
Australian Office Action, Examiner's Report No. 2, dated May 24, 2011 for Application No. AU 2005203222.
Australian Office Action, Examiner's First Report, dated Jan. 10, 2012 for Application No. AU 2006222752.
Australian Office Action, Examiner's First Report, dated Sep. 28, 2011 for Application No. AU 2006222758.
Australian Office Action, Examiner's First Report, dated Nov. 8, 2011 for Application No. AU 2006222763.
Canadian Office Action dated May 3, 2012 for Application No. 2,512,948.
Canadian Office Action dated Aug. 29, 2011 for Application No. 2,512,960.
Canadian Office Action dated May 28, 2012 for Application No. 2,512,977.
Canadian Office Action dated May 23, 2012 for Application No. 2,513,472.
Canadian Office Action dated Jan. 2, 2013 for Application No. 2,513,472.
Canadian Office Action dated May 23, 2012 for Application No. 2,513,511.
Canadian Office Action dated Jan. 21, 2013 for Application No. 2,513,511.
Canadian Office Action dated Jun. 14, 2012 for Application No. 2,514,214.
Canadian Office Action dated Aug. 30, 2011 for Application No. 2,514,274.
Canadian Office Action dated Apr. 29, 2013 for Application No. 2,561,234.
Canadian Office Action dated Apr. 4, 2013 for Application No. 2,561,241.
Canadian Office Action dated Dec. 14, 2012 for Application No. 2,561,472.
Canadian Office Action dated May 3, 2013 for Application No. 2,561,473.
Canadian Office Action dated Apr. 29, 2013 for Application No. 2,561,544.
Canadian Office Action dated Mar. 8, 2013 for Application No. 2,561,653.
Chinese Office Action, Notification of the First Office Action, dated Dec. 26, 2008 for Application No. CN 200510087335.2.
Chinese Office Action, Notification of the First Office Action, dated May 23, 2008 for Application No. CN 200510089519.2.
Chinese Office Action, Notification of the First Office Action, dated Oct. 10, 2008 for Application No. CN 200510089529.6.
Chinese Office Action, Notification of the First Office Action, dated Jul. 24, 2009 for Application No. CN 200610146377.3.
Chinese Office Action, Notification of the First Office Action, dated Jul. 24, 2009 for Application No. CN 200610146378.8.
Chinese Office Action, Notification of the First Office Action, dated Aug. 7, 2009 for Application No. CN 200610146380.5.
Chinese Office Action, Notification of the First Office Action, dated Oct. 23, 2009 for Application No. CN 200610147753.5.
Chinese Office Action, Notification of the First Office Action, dated Aug. 7, 2009 for Application No. CN 200610144755.4.
EP Communication dated Oct. 29, 2007 for Application No. EP 06255064.5.
EP Communication dated Oct. 29, 2007 for Application No. EP 06255053.8.
EP Communication dated Oct. 29, 2007 for Application No. EP 06255057.9.
European Search Report dated Nov. 15, 2006 for Application No. EP 06255061.
Indian Office Action, First Examination Report, dated Dec. 5, 2013 for Application No. 641/KOL/2005.
Japanese Office Action, Notification of Reasons for Refusal, dated Feb. 22, 2011 for Application No. JP 2005-216940.
Japanese Office Action, Notification of Reasons for Refusal, dated Jan. 18, 2011 for Application No. JP 2005-216963.
Japanese Office Action, Notification of Reasons for Refusal, dated Dec. 1, 2011 for Application No. JP 2005-216963.
Japanese Office Action, Notification of Reasons for Refusal, dated Mar. 1, 2011 for Application No. JP 2005-216972.
Japanese Office Action, Notification of Reasons for Refusal, dated Mar. 1, 2011 for Application No. JP 2005-217069.
Japanese Office Action, Notification of Reasons for Refusal, dated Mar. 8, 2011 for Application No. JP 2005-217076.
Japanese Office Action, Notification of Reasons for Refusal, dated Mar. 8, 2011 for Application No. JP 2005-217080.
Japanese Office Action, Notification of Reasons for Refusal, dated Mar. 8, 2011 for Application No. JP 2005-217107.
Japanese Office Action, Notification of Reasons for Refusal, dated Mar. 8, 2011 for Application No. JP 2005-217089.
Japanese Office Action, Notification of Reasons for Refusal, dated Aug. 18, 2011 for Application No. JP 2006-267232.
Japanese Office Action, Notification of Reasons for Refusal, dated Aug. 18, 2011 for Application No. JP 2006-267238.
Japanese Office Action, Notification of Reasons for Refusal, dated Oct. 31, 2011 for Application No. JP 2005-267245.
Japanese Office Action, Notification of Reasons for Refusal, dated Jul. 3, 2012 for Application No. JP 2006-267245.
Japanese Office Action, Notification of Reasons for Refusal, dated Aug. 18, 2011 for Application No. JP 2006-267291.
Japanese Office Action, Notification of Reasons for Refusal, dated Aug. 18, 2011 for Application No. JP 2006-267300.
Japanese Office Action, Notification of Reasons for Refusal, dated Aug. 18, 2011 for Application No. JP 2006-267315.
Opposition, *Covidien Surgical* v. *Ethicon Endo-Surgery Inc.* against Application No. EP 06255058.7 dated Oct. 6, 2010.
Russian Office Action dated Jun. 22, 2009 for Application No. 2005123950.
Russian Office Action dated Jun. 22, 2009 for Application No. 2005123962.
Russian Office Action dated Jun. 22, 2009 for Application No. 2005123973.
Russian Office Action dated Jun. 22, 2009 for Application No. 2005123979.
Russian Office Action dated Jun. 22, 2009 for Application No. 2005123980.
Notice of Allowance dated Nov. 13, 2008 for U.S. Appl. No. 11/082,495.
Restriction Requirement dated Sep. 5, 2008 for U.S. Appl. No. 11/092,053.

(56) References Cited

OTHER PUBLICATIONS

Non-Final Rejection dated Dec. 29, 2008 for U.S. Appl. No. 11/092,053.
Final Rejection dated Sep. 2, 2009 for U.S. Appl. No. 11/092,053.
Non-Final Rejection dated Feb. 8, 2010 for U.S. Appl. No. 11/092,053.
Non-Final Rejection dated Jul. 28, 2010 for U.S. Appl. No. 11/092,053.
Final Rejection dated Jan. 10, 2011 for U.S. Appl. No. 11/092,053.
Non-Final Rejection dated Apr. 27, 2011 for U.S. Appl. No. 11/092,053.
Final Rejection dated Jun. 2, 2011 for U.S. Appl. No. 11/092,053.
Notice of Allowance dated Jul. 11, 2011 for U.S. Appl. No. 11/092,053.
Restriction Requirement dated Feb. 19, 2009 for U.S. Appl. No. 11/095,428.
Non-Final Rejection dated Jun. 3, 2009 for U.S. Appl. No. 11/095,428.
Final Rejection dated Dec. 14, 2009 for U.S. Appl. No. 11/095,428.
Non-Final Rejection dated Apr. 26, 2010 for U.S. Appl. No. 11/095,428.
Notice of Allowance dated Oct. 6, 2010 for U.S. Appl. No. 11/095,428.
Notice of Allowance dated Sep. 19, 2008 for U.S. Appl. No. 11/096,096.
Notice of Allowance dated Dec. 3, 2008 for U.S. Appl. No. 11/181,046.
Notice of Allowance dated Jun. 29, 2009 for U.S. Appl. No. 11/240,836.
Notice of Allowance dated Oct. 9, 2009 for U.S. Appl. No. 11/240,836.
Notice of Allowance dated Jan. 28, 2010 for U.S. Appl. No. 11/240,836.
Notice of Allowance dated May 17, 2010 for U.S. Appl. No. 11/240,836.
Non-Final Rejection dated Nov. 23, 2010 for U.S. Appl. No. 12/696,397.
Non-Final Rejection dated Sep. 16, 2011 for U.S. Appl. No. 12/696,397.
Final Rejection dated May 5, 2011 for U.S. Appl. No. 12/696,397.
Notice of Allowance dated Dec. 16, 2011 for U.S. Appl. No. 12/696,397.
Notice of Allowance dated Mar. 29, 2012 for U.S. Appl. No. 12/696,397.
Non-Final Rejection dated Sep. 10, 2012 for U.S. Appl. No. 13/544,128.
Final Rejection dated Jan. 3, 2013 for U.S. Appl. No. 13/544,128.
Notice of Allowance dated Apr. 12, 2013 for U.S. Appl. No. 13/544,128.
U.S. Appl. No. 14/175,139, filed Feb. 7, 2014.
U.S. Appl. No. 14/175,148, filed Feb. 7, 2014.

* cited by examiner

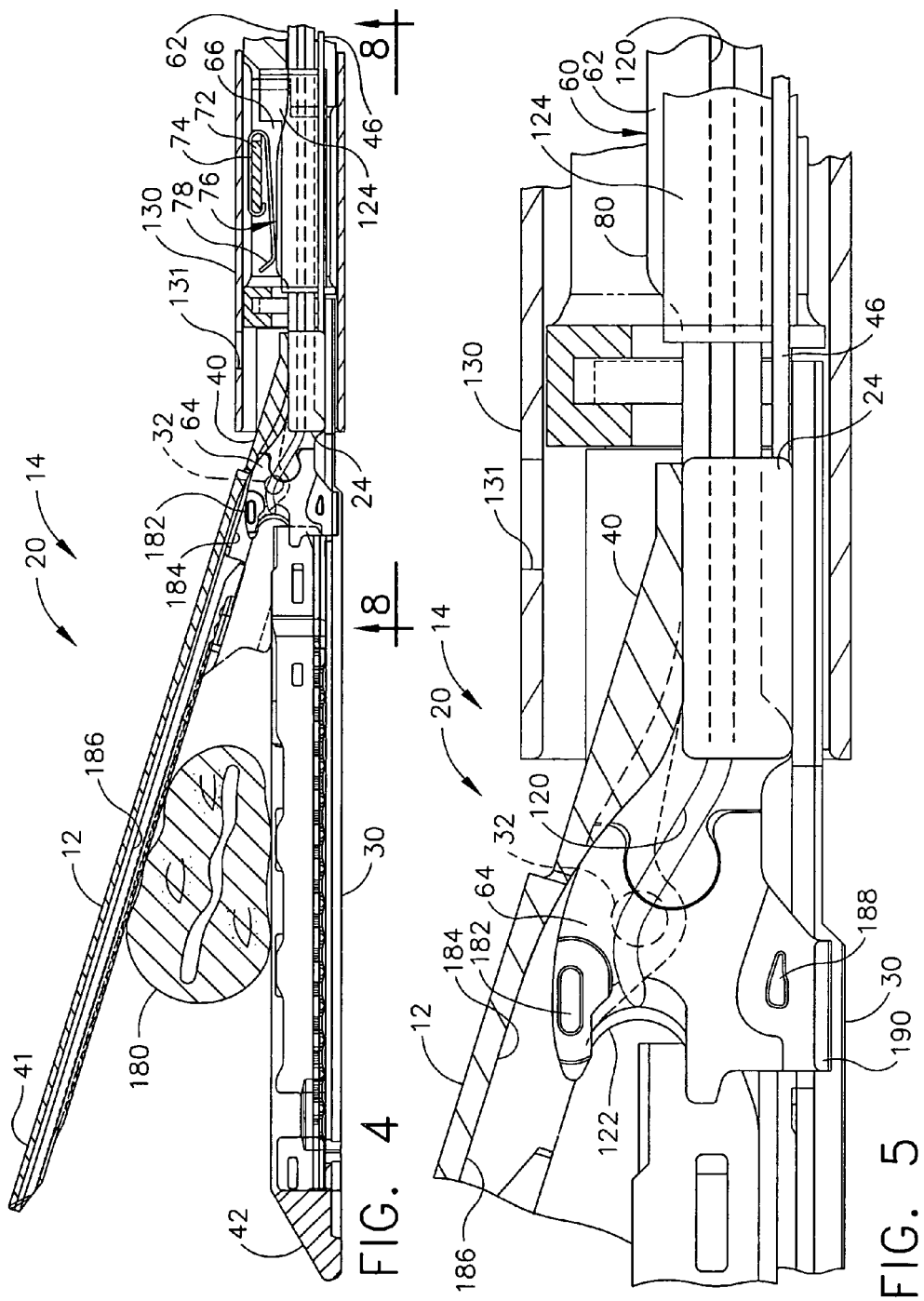

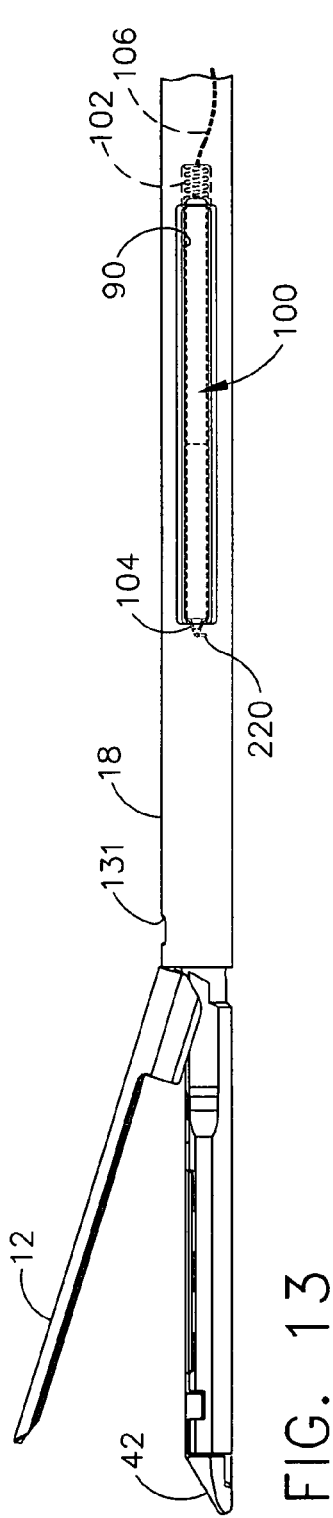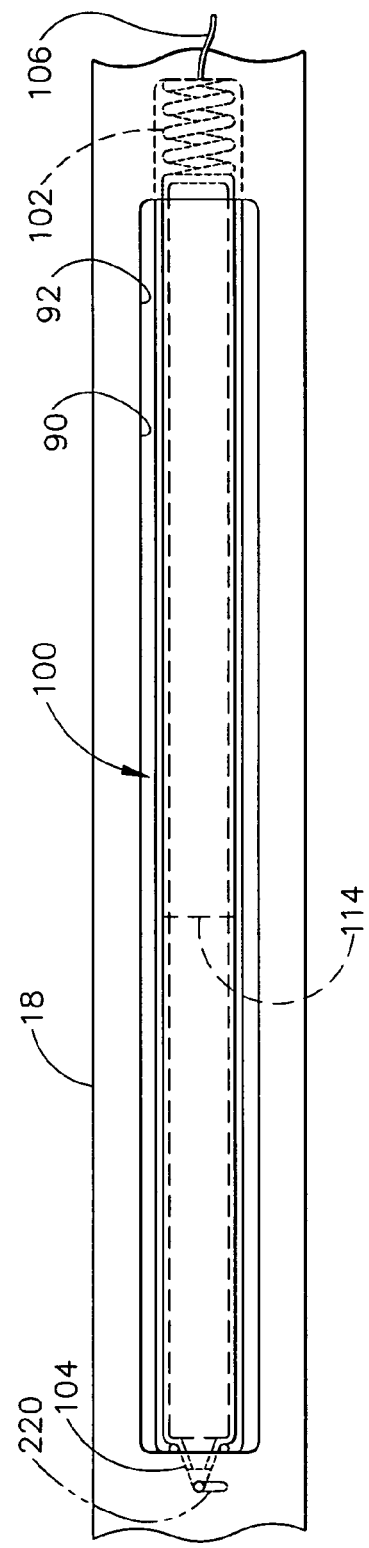

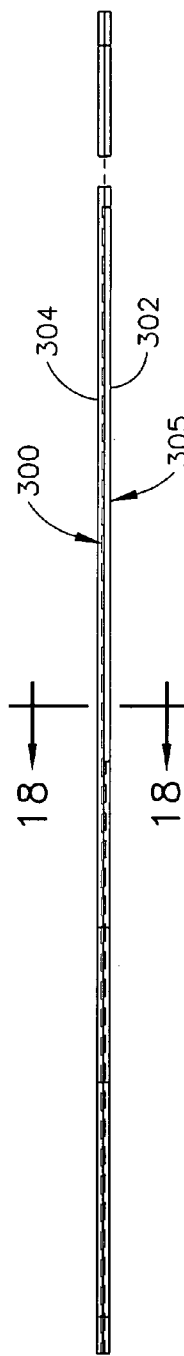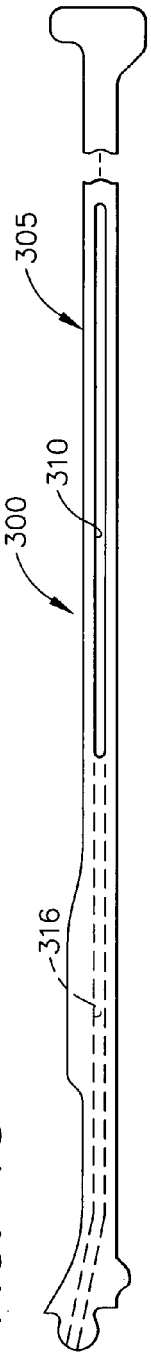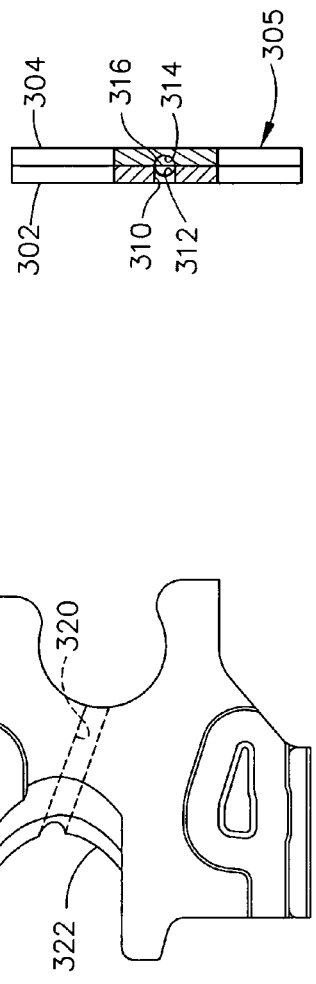

SURGICAL STAPLING INSTRUMENT HAVING AN ELECTROACTIVE POLYMER ACTUATED MEDICAL SUBSTANCE DISPENSER

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004. This application is related to commonly owned U.S. patent application Ser. No. 11/082,495, entitled "SURGICAL INSTRUMENT INCORPORATING AN ELECTRICALLY ACTUATED ARTICULATION MECHANISM" filed on 17 Mar. 2005, the disclosure of which is hereby incorporated by reference in its entirety.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications, described in U.S. Pat. No. 5,465,895, advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

These minimally invasive surgical instruments have been widely used and have proven to be a significant advancement over traditional open surgical techniques. It would be desirable to incorporate yet additional features and capabilities. For instance, in Int'l Pat. Appln. WO 03/094743 A1, a wound closure material applicator assembly is described that dispenses at a needle in a knife of a surgical stapling apparatus as the knife is moved to sever tissue. Dispensing is actuated by reservoir compressed by the firing handle or by a separate syringe.

While such an ability to apply a medical substance upon tissue simultaneously with severing and stapling may be desirable, it is believed that it would be desirable to not impose a greater force to fire requirement upon the surgeon, or to require another detached device be actuated.

Consequently, a significant need exists for a surgical instrument with an improved ability to dispense a medical substance.

BRIEF SUMMARY OF THE INVENTION

The invention overcomes the above-noted and other deficiencies of the prior art by providing a surgical instrument that is suitable for minimally invasive surgical procedures by having a handle that positions an end effector through a surgical opening via an elongate shaft. An electrically controlled medical substance delivery mechanism incorporated through the elongate shaft to the end effector enhances the utility and effectiveness of the instrument. Thereby, numerous therapeutic treatments may be precisely applied onto the tissue as it is severed so that post operative recovery and complications are reduced.

In one aspect of the invention, this end effector includes opposing jaws for clamping tissue. A firing bar is received for reciprocating longitudinal motion in the elongate shaft to transfer a firing motion from the handle. A cutting surface distally attached to the firing bar is pushed by this firing motion to sever the clamped tissue in the end effector. Enhancing healing of the severed tissue, a fluid passage is advantageously defined longitudinally in the firing bar to the cutting surface. An electrical fluid dispenser in communication with the fluid passage responds to a dispensing signal from control circuitry to dispense a medical substance along the fluid passage to the cutting surface.

In another aspect of the invention, a surgical instrument includes a fluid passage to the end effector. A syringe cylinder in the surgical instrument has a portion of its internal volume filled with a medical substance. Control circuitry generates a dispensing signal to an electroactive polymer plunger in the syringe cylinder. The electroactive polymer plunger expands into the internal volume to dispense the medical substance through a dispensing opening through the fluid passage to the end effector. Thereby, a number of minimally invasive surgical procedures may be accompanied by simultaneous or selective dispensing of a medical substance at the site of the surgical treatment. Moreover, the characteristics of electroactive polymers lends themselves to a reliable instrument with significant shelf life prior to use.

In yet another aspect of the invention, a surgical instrument that staples and severs clamped tissue benefits from the simultaneous electrically actuated dispensing of a medical substance at a cutting surface of a firing bar. Thereby, trauma to the tissue due to the severing and stapling may be mitigated by a capability of dispensing directly onto this location in a timely fashion.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

in an open position and an electroactive polymer (EAP) medical substance dispensing shaft.

Figure 1:
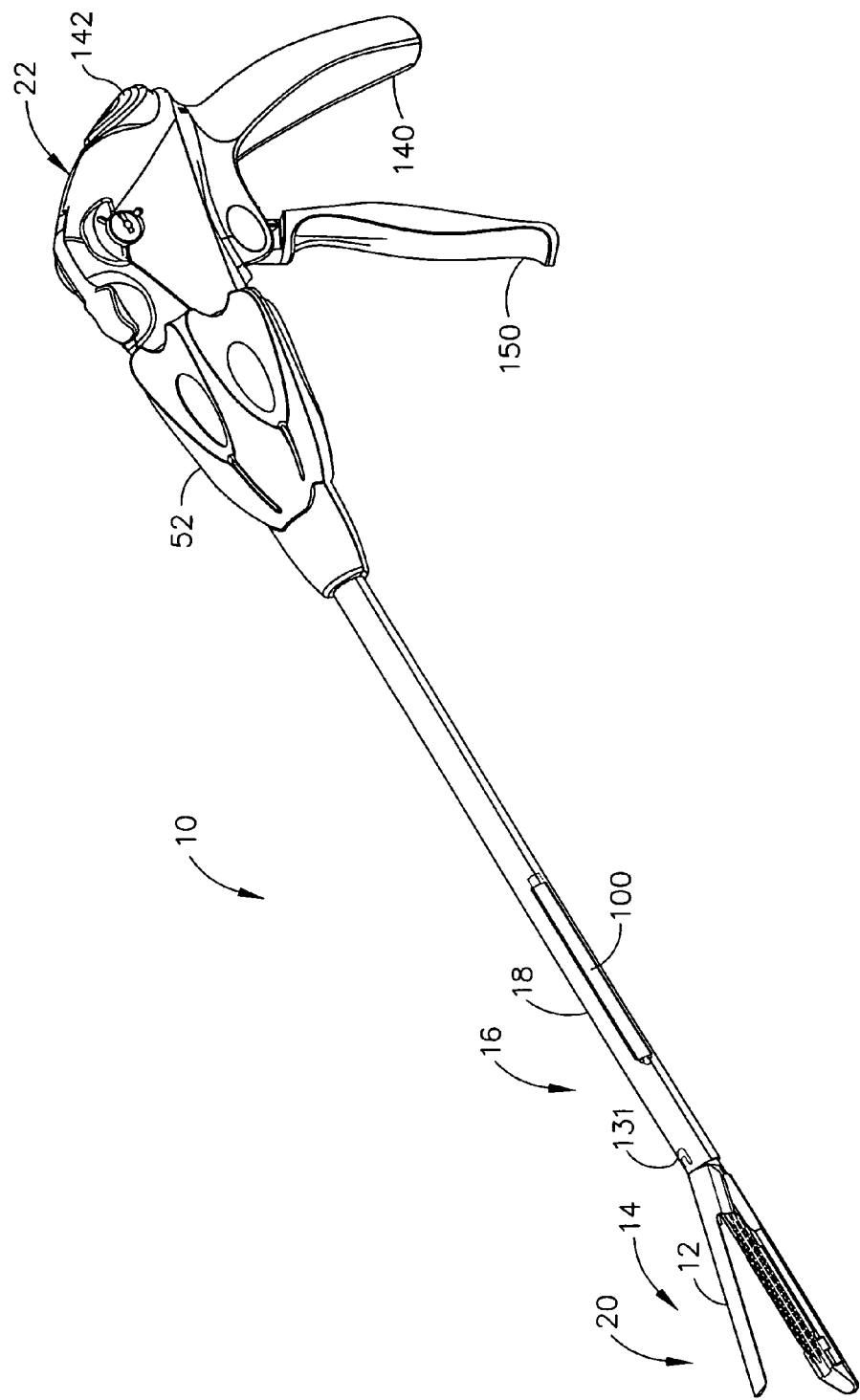
FIG. 1 is a perspective view of a surgical stapling and severing instrument having a fluid actuated upper jaw (anvil)
Figure 2:
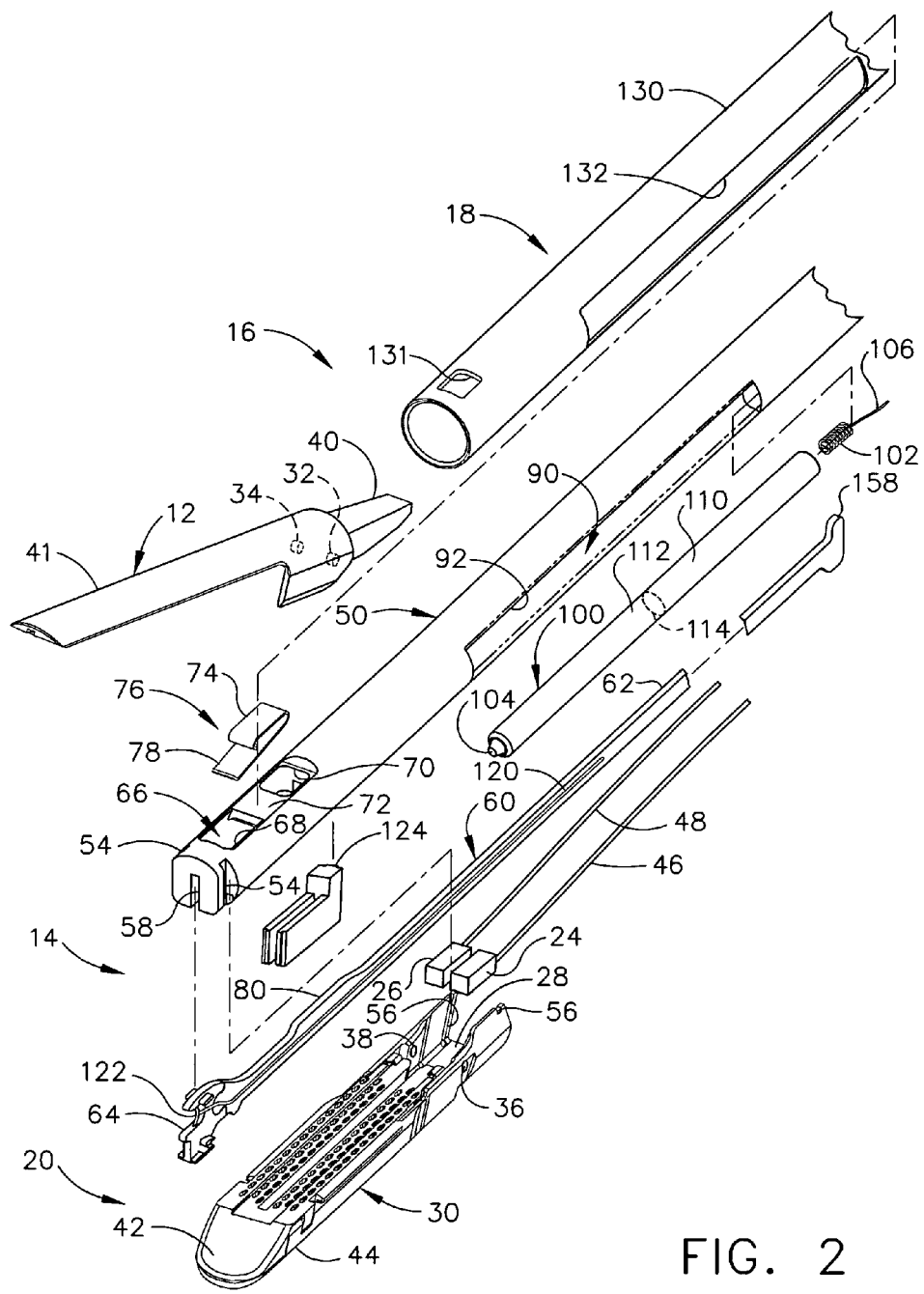

FIG. 2 is a disassembled perspective view of an implement portion of the surgical stapling and severing instrument of FIG. 1.

Figure 3:
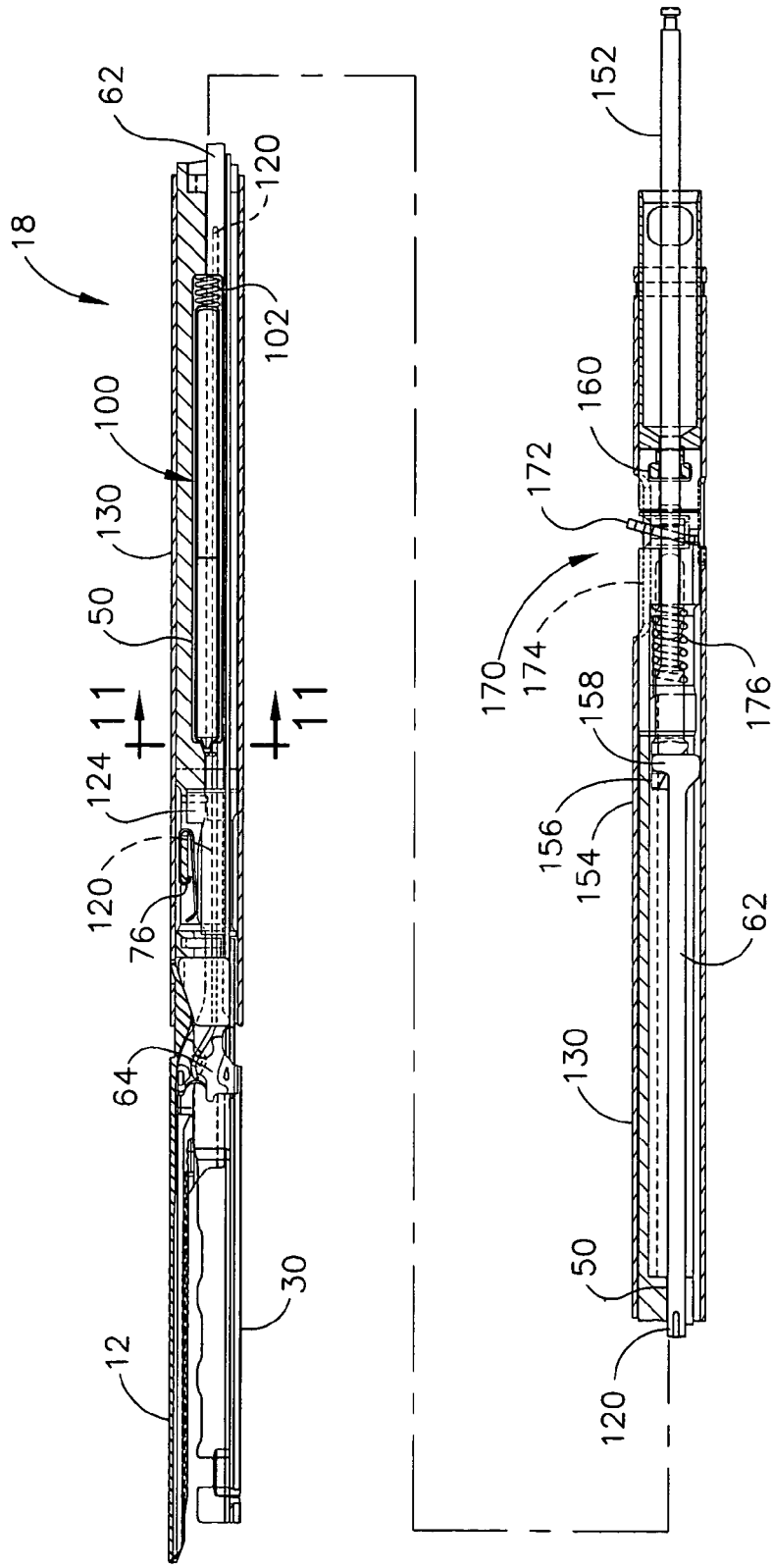

FIG. 3 is left side view in a elevation of the implement portion of the surgical stapling and severing instrument of FIG. 1 taken in cross section generally through a longitudinal axis and passing through an offset EAP syringe and receptacle that is in fluid communication with a dispensing groove in an E-beam firing bar.

FIG. 4 is a left side detail view in elevation of a distal portion of the implement portion of the surgical stapling and severing instrument of FIG. 1 taken in cross section generally through the longitudinal axis thereof but showing a laterally offset fluid bladder actuator opening the anvil.

FIG. 5 is a left side detail view of an E-beam firing bar incorporating medical substance ducting.

Figure 6:
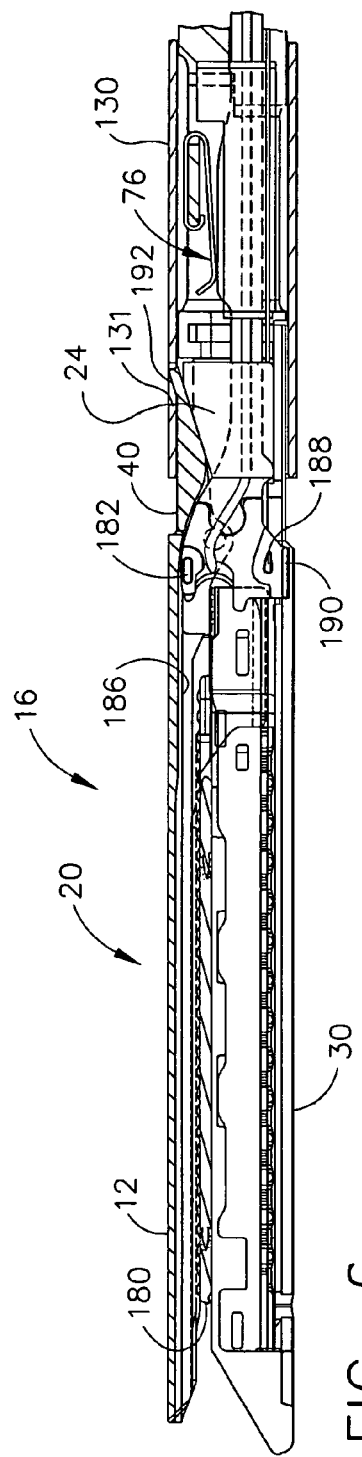

FIG. 6 is a left side detail view in elevation of the distal portion of the implement portion of the surgical stapling and severing instrument of FIG. 4 taken in cross section generally through the longitudinal axis thereof with the anvil closed.

Figure 7:
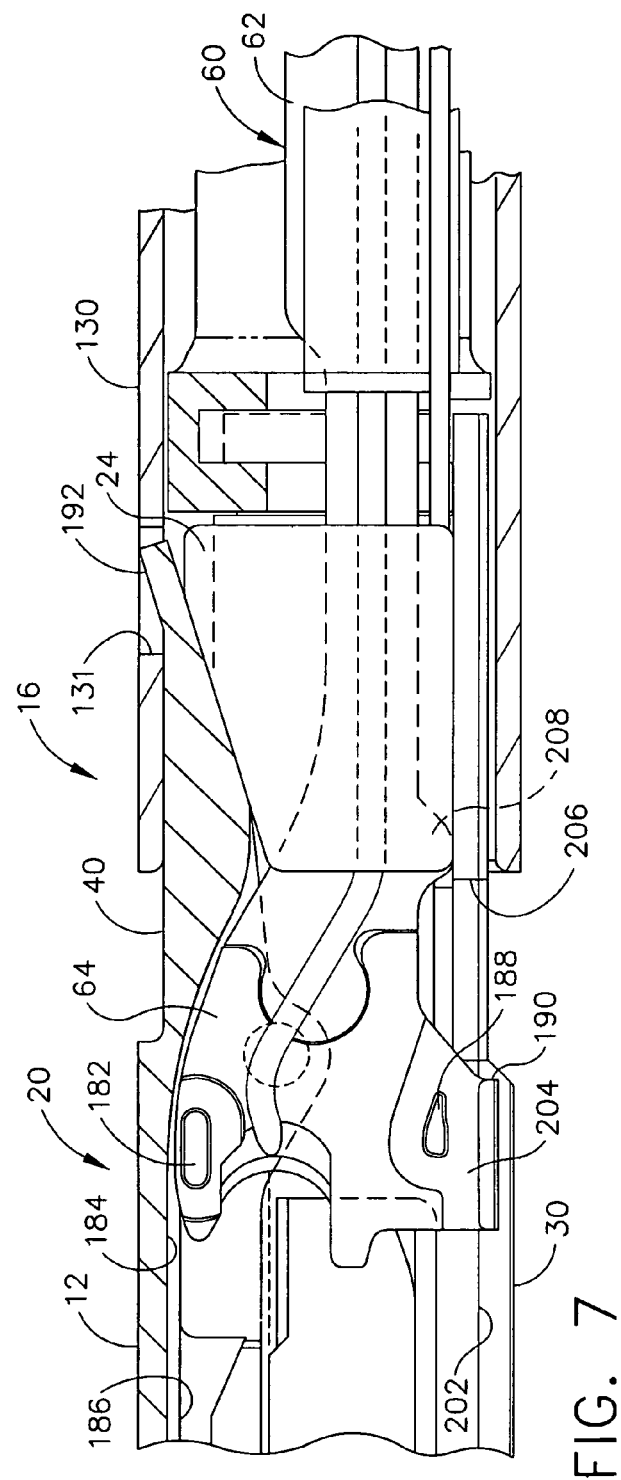

FIG. 7 is a left side detail view of the E-beam firing bar of FIG. 6.

Figure 8:
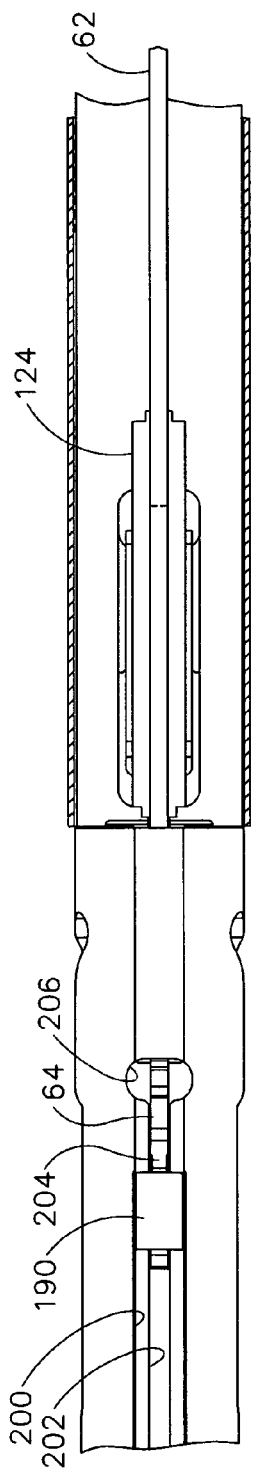

FIG. 8 is a top detail view of a joined portion of a lower jaw (staple channel) of the end effector and elongate shaft taken in cross section through the lines 8-8 depicting guidance to the E-beam firing bar.

Figure 9:
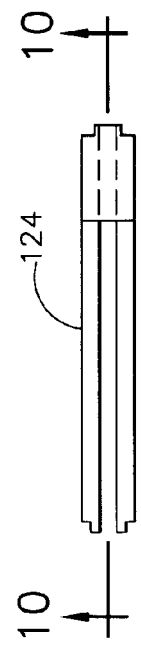

FIG. 9 is a front view of a firing bar guide of the implement portion of the surgical stapling and severing instrument of FIG. 2.

Figure 10:
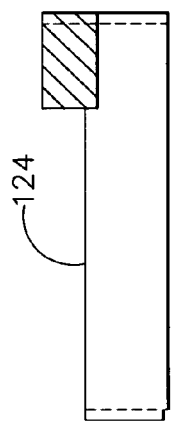

FIG. 10 is a left side view of the firing bar guide of FIG. 9 taken in cross section along lines 9-9.

Figure 11:
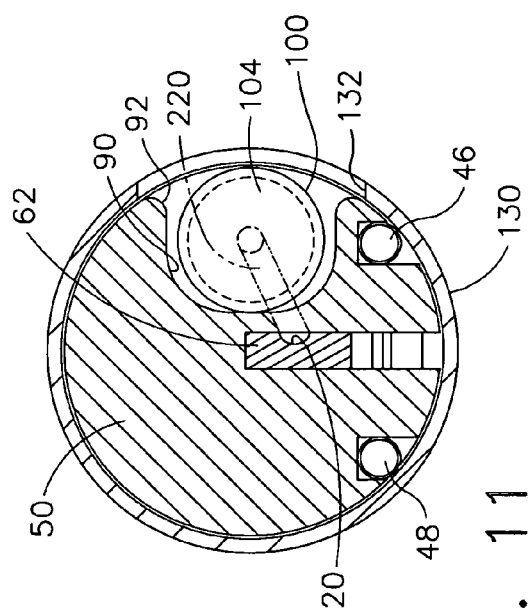

FIG. 11 is a front view in elevation of the elongate shaft of the surgical stapling and severing instrument of FIG. 3 taken along lines 11-11 taken through a distal end of the EAP medical substance syringe.

Figure 12:
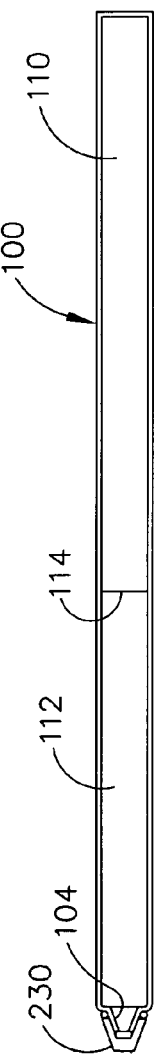

FIG. 12 is a left side view of the EAP medical substance syringe of FIG. 11.

FIG. 13 is a left side view of the implement portion of the surgical stapling and severing instrument of FIG. 1 partially cut away to show proximal mountings for the EAP medical substance syringe.

FIG. 14 is a left side detail view of the EAP medical substance syringe and receptacle of the elongate shaft of the surgical stapling and severing instrument of FIG. 13.

FIG. 15 is a top view of the firing bar of the surgical stapling and severing instrument of FIG. 2.

FIG. 16 is a left side view of a laminate firing bar showing an internal fluid path in phantom for the surgical stapling and severing instrument of FIG. 1.

FIG. 17 is a left side detail view of an alternate E-beam showing an internal fluid path in phantom showing an internal fluid path in phantom.

FIG. 18 is a front view in elevation of the laminate firing bar of FIG. 15 taken in cross section along line 18-18 through a proximal open groove of a fluid path.

DETAILED DESCRIPTION OF THE INVENTION

Turning to the Drawings, wherein like numerals denote like components throughout the several views, in FIGS. 1-2, a surgical stapling and severing instrument 10 that is capable of practicing the unique benefits of the present invention, including both fluid actuation (e.g., opening, closing/clamping) of an upper jaw (anvil) 12 of an end effector 14 as well as dispensing a medical substance onto tissue as severed. Fluid actuation of the end effector 14 provides a range of design options that avoid some design limitations of traditional mechanical linkages. For example, instances of binding or component failure may be avoided. Further, dispensing liquids onto severed tissue allows for a range of advantageous therapeutic treatments to be applied, such as the application of anesthetics, adhesives, cauterizing substances, antibiotics, coagulant, etc.

With particular reference to FIG. 2, the surgical stapling and severing instrument 10 includes an implement portion 16 formed by an elongate shaft 18 and the end effector 14, depicted as a stapling assembly 20. The surgical stapling and severing instrument 10 also includes a handle 22 (FIG. 1) attached proximally to the shaft 18. The handle 22 remains external to the patient as the implement portion 16 is inserted through a surgical opening, or especially a cannula of a trocar that forms a pneumoperitoneum for performing a minimally invasive surgical procedure.

Left and right fluid bladders (lift bags) 24, 26 are supported within an aft portion 28 of a staple channel 30. The anvil 12 includes a pair of inwardly directed lateral pivot pins 32, 34 that pivotally engage outwardly open lateral pivot recesses 36, 38 formed in the staple channel 30 distal to the aft portion 28. The anvil 12 includes a proximally directed lever tray 40 that projects into the aft portion 28 of the staple channel 30 overtop and in contact with the fluid bladders (lift bags) 24, 26 such that filling the fluid bladders 24, 26 causes a distal clamping section 41 of the anvil 12 to pivot like a teeter-totter toward a staple cartridge 42 held in a distal portion 44 of the staple channel 30. Evacuation and collapse of the fluid bladders 24, 26, or some other resilient feature of the end effector 14, causes the anvil 12 to open. Left and right fluid conduits 46, 48 communicate respectively with the left and right fluid bladders 24, 26 to bi-directionally transfer fluid for actuation. It should be appreciated that applications consistent with the present invention may include a mechanical actuation in the handle 22 (e.g., closure trigger) (not shown) wherein the user depresses a control that causes closure and clamping of the end effector 12.

It will be appreciated that the terms "proximal" and "distal" are used herein with reference to a clinician gripping a handle of an instrument. Thus, the staple applying assembly 20 is distal with respect to the more proximal handle 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

With particular reference to FIG. 2, the elongate shaft 18 includes a frame 50 whose proximal end is rotatably engaged to the handle 22 (FIG. 1) such that a rotation knob 52 rotates the frame 50 along with the end effector 14. A distal end of the frame 50 has lateral recesses 54 that engage a proximal lip 56 of the staple channel 30. The frame 50 includes a laterally centered, bottom firing slot 58 that passes longitudinally through the frame 50 for receiving a two-piece firing bar 60 comprised of a firing bar 62 with a distally attached E-beam 64, the latter translating within the staple applying assembly 20 to sever and staple tissue. A distal portion of the frame 50 includes an upper cavity 66 whose distal and proximal ends communicate through distal and proximal apertures 68, 70, defining there between a cross bar 72 over which a distally projecting clip 74 of a clip spring 76 engages with a lower spring arm 78, distally and downwardly projecting through the upper cavity 66 to bias the firing bar 62 downwardly into engagement with the staple channel 30, especially when the lower spring arm 78 encounters a raised portion 80 on the firing bar 62.

Medical substance dispensing is integrated into the elongate shaft 18 by including a laterally offset cylindrical cavity 90 formed in the frame 50 that communicates along its longitudinal length to the outside via a rectangular aperture 92 that is slightly shorter than an electroactive polymer (EAP) syringe 100 that is inserted through the aperture 92 into the cylindrical cavity 90. A proximal portion of the cylindrical cavity 90 contains a longitudinally aligned compression spring 102 that urges a distal dispensing cone 104 of the EAP syringe 100 distally into sealing contact with the frame 50 and allows translation for insertion and removal of the EAP syringe 100. An electrical conductor 106 passes through the frame 50 and is attached to the compression spring 102, which is also formed of an electrically conductive metal. An aft portion of the EAP syringe 100 is conductive and contacts the spring 102 to form a cathode to an EAP actuator 110 held in a proximal portion of the EAP syringe 100. It will be appreciated that another conductor, perhaps traveling with the conductor 106, also electrically communicates to the EAP actuator 110 to serve as the anode.

When activated, the EAP actuator 110 longitudinally expands, serving as a plunger to dispel a medical substance 112 in a distal portion of the EAP syringe 100 through the distal dispensing cone 104. Insofar as the EAP actuator 110 laterally contracts to compensate for its longitudinal expansion, a plunger seal 114 maintains a transverse seal within the EAP syringe 100. An vent (not shown), such as around conductor 106 allows air to refill the EAP syringe 100 behind the plunger seal 114 as the medical substance 112 is dispensed. The vent may rely upon the surface tension of the medical substance 112 to avoid leaking or be a one-way valve. As described below, the medical substance 112 is conducted by the frame 50 to a lateral fluid groove 120 that is formed in the firing bar 62 and the E-beam 64 to direct the medical substance to a cutting surface 122 of the E-beam 64. The frame slot 58 is sized to seal the lateral fluid groove 120. The portion of the lateral fluid groove 120 that is positioned under the spring clip 76 is sealed by a firing bar guide 124. In the illustrative version, an outer sheath 130 encompasses the frame 50 and proximally projecting lever tray 40 of the anvil 12. A top distal opening 131 allows closing of the anvil 12.

An outer rectangular aperture 132 of the outer sheath 130 is sized and longitudinally positioned to correspond to the rectangular aperture 92 formed in frame 50. In some applications, the outer sheath 130 may be rotated to selectively align the rectangular aperture 92 with the outer rectangular aperture 132 for insertion or removal of the EAP syringe 100. It should be appreciated that in some applications that the EAP syringe 100 may be integrally assembled into an elongate shaft that does not allow for selecting a desired medical substance. For instance, a disposable implement portion with an integral staple cartridge and medical dispensing reservoir may be selected by the clinician as a unit. It is believed that allowing insertion at the time of use, though, has certain advantages including clinical flexibility in selecting a medical substance (e.g., anesthetics, adhesives, antibiotics, cauterizing compound, etc.) and extending the shelf life/simplifying storage and packaging of the implement portion 16.

In the illustrative version, an elongate stack of many disk-shaped EAP layers are aligned longitudinally and configured to expand along this longitudinal axis. Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from IV to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types of EAPs and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually made up of a central wire core and a conductive outer sheath that also serves to contain the ionic fluid that surrounds the fiber bundles. An example of a commercially available fiber EAP material, manufactured by Santa Fe Science and Technology and sold as PANION™ fiber, is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is from Artificial Muscle Inc, a division of SRI Laboratories. Plate EAP material is manufactured by EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. The laminate version may also be adhered to either side of a flexible plate. When one side of the flexible plate EAP is energized, it expands flexing the plate in the opposite direction. This allows the plate to be flexed in either direction, depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30%, utilizing much higher voltages.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers there between to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Returning to FIG. 1, the handle 22 controls closure of the anvil 12, firing of the two-piece firing bar 60 (FIG. 2), and dispensing of the medical substance. In an illustrative version, a pistol grip 140 may be grasped and a thumb button 142 depressed as desired to control closure of the anvil 12. The thumb button 142 provides a proportional electrical signal to an EAP dispensing actuator not shown) similar to the EAP syringe 100 to transfer fluid through the conduits 46, 48 to the fluid bladders 24, 26 to close the anvil 12 (FIG. 2). When the thumb button 142 is fully depressed, a mechanical toggle lock (not shown) engages to hold the thumb button 142 down until a full depression releases the toggle lock for releasing the thumb button 142. Thus, when the thumb button 142 is held down, the surgeon has a visual indication that the end effector 14 is closed and clamped, which may be maintained in this position by continued activation of an EAP dispensing actuator or by a locking feature. For instance, control circuitry may sense movement of the thumb button 142, causing a normally closed EAP shutoff valve (not shown) to open that communicates between the EAP dispensing actuator and the conduits 46, 48. Once movement ceases, the EAP shutoff valve is allowed to close again, maintaining the anvil 12 position. In addition, a manual release could be incorporated to defeat such a lockout to open the anvil 12.

As an alternative, a closure trigger (not shown) or other actuator may be included that bi-directionally transfers fluid to the fluid bladders 24, 26 as described in commonly owned U.S. patent application Ser. No. 11/061,908 entitled "SURGICAL INSTRUMENT INCORPORATING A FLUID TRANSFER CONTROLLED ARTICULATION MECHANISM" to Kenneth Wales and Chad Boudreaux, filed on 18 Feb., 2005, the disclosure of which is hereby incorporated by reference in its entirety. A number of such fluid actuators for articulation of a pivoting shaft are described that may be adapted for closing the anvil 12. To take full advantage of the differential fluid transfer described for several of these versions, it should be appreciated that an opposing lift bag (not shown) may be placed above the lever tray 40 of the anvil 12 to assert an opening force as the left and right fluid bladders (lift bags) 24, 26 collapse.

With particular reference to FIG. 3, the handle 22 includes a firing trigger 150 (FIG. 1) that is drawn proximally toward the pistol grip 140 to cause a firing rod 152 to move distally in a proximal portion 154 of the elongate shaft 18. A distal bracket 156 of the firing rod 152 engages an upward proximal hook 158 of the firing bar 62. A dynamic seal 160 within the frame 50 seals to the firing rod 152 so that the implement portion 16 is pneumatically sealed when inserted into an insufflated abdomen.

An anti-backup mechanism 170 of the firing rod 152 may be advantageously included for a handle 22 that includes a multiple stroke firing trigger 150 and a retraction biased firing mechanism coupled to the firing rod 152 (not shown). In particular, an anti-backup locking plate 172 has the firing rod 152 pass through a closely fitting through hole (not shown) that binds when a retracting firing rod 152 tips the lock plate 172 backward as shown with the bottom of the locking plate 172 held in position within the frame 50. An anti-backup cam sleeve 174 is positioned distal to the anti-backup locking plate 172 and urged into contact by a more distal compression spring 176 through which the firing rod 152 passes and that is compressed within the frame 50. It should be appreciated that mechanisms in the handle 22 may manually release the anti-backup mechanism 170 for retraction of the firing rod 152.

In FIGS. 4-5, the end effector 14, which in the illustrative version is a staple applying assembly 20, is opened by having fluid bladder 24 deflated, drawing down lever tray 40 of the anvil 12, which pivots about pin 32 raising distal clamping section 41 thereby allowing positioning body tissue 180 between the anvil 12 and staple cartridge 42. The E-beam 64 has an upper pin 182 that resides within an anvil pocket 184 allowing repeated opening and closing of the anvil 12. An anvil slot 186 formed along the length of the anvil 12 receives the upper pin 182 when the anvil 12 is closed and the two piece firing bar 60 is distally advanced. A middle pin 188 slides within the staple cartridge 42 above the staple channel 30 in opposition to a bottom pin or foot 190 that slides along a bottom surface of the staple channel 30.

In FIGS. 6-7, the staple applying assembly 20 has been closed by expanding the fluid bladder (lift bag) 24, raising the lever tray 40 of the anvil 12 until flush with the outer sheath 130, with a proximal upwardly bent tip 192 of the lever tray 40 allowed to enter the top distal opening 131. This bent tip 192 in combination with the opening 131, advantageously allows greater radial travel for the anvil 12 as well as presenting an abutting surface rather than a piercing tip to the underlying fluid bladder 24. When the anvil 12 is closed, the upper pin 182 is aligned with the anvil slot 186 for firing and the tissue 180 is flattened to a thickness appropriate for severing and stapling.

In FIGS. 7-8, the E-beam 64 is cut away to show its bottom foot 190 riding along a downwardly open laterally widened recess 200 that communicates with a narrow longitudinal slot 202 through which a vertical portion 204 of the E-beam 64 passes. A proximal aperture 206 to the narrow longitudinal slot 202 allows an assembly entrance for the lower foot 190. A bottom bump 208 is positioned on the firing bar 62 to drop into the proximal aperture 206 during an initial portion of firing travel under the urging of the clip spring 76 (FIG. 6) against the raised portion 80 of the firing bar 62 for proper engagement and for possible interaction with an end effector firing lockout mechanism (not shown). Also, this position allows for the end effector 14 to be pinched shut to facilitate insertion through a surgical entry point such as a cannula of a trocar (not shown). With reference to FIGS. 8-10, the firing bar guide 124 laterally contacts a portion of the firing bar 62 to close the corresponding portion of the lateral fluid groove 120. In FIG. 11, the EAP syringe 100 in the cylindrical cavity 90 has its distal dispensing cone 104 communicating with a radial fluid passage 220 formed in the frame 50 that communicates in turn with the lateral fluid groove 120. In FIG. 12, before installation in the surgical stapling and severing instrument 10, the EAP syringe 100 may be advantageously sealed with a disposable cap 230. In FIGS. 13-14, the EAP syringe 100 is shown without the disposable cap 230 and urged by spring 102 distally to engage the distal dispensing cone 104 into communication with the radial fluid passage 220.

It should be appreciated that one or more sensor in the surgical stapling and severing instrument 10 may sense a firing condition (e.g., movement of firing bar or mechanism coupled to the firing bar, position of the firing trigger, a separate user control to dispense, etc.) and activate dispensing control circuitry to effect dispensing.

In FIGS. 15-18, an alternate two-piece firing bar 300 is formed from longitudinally laminated left half and right half firing bar portions 302, 304 that form a firing bar 305 and attached to an E-beam 309. Thereby, fluid transfer down the firing bar 300 may be further constrained. In particular, a left side fluid groove 310 in the left half firing bar portion 302 transitions distally to a pair of aligned internal fluid grooves 312, 314 respectively in the left and right half firing bar portions 302, 304, defining an internal fluid passage 316. Since the E-beam 309 is laterally thicker and of short longitudinal length, a drilled fluid passage 320 is formed therein between a cutting surface 322 and an aft edge aligned to communicate with the internal fluid passage 316.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a non-articulating shaft is described herein for clarity, it should be appreciated that medical substance dispensing may be incorporated into an articulating shaft. In addition, fluid conduits may be incorporated that pass through an articulation joint of a shaft to fluid bladder actuators that close an end effector.

As another example, while both medical substance dispensing and fluid actuated anvil closing are illustrated herein, applications consistent with aspects of the invention may include either of these features. Further, for applications in which an adhesive and/or cauterizing medical substance is dispensed, it should be appreciated that features such as staples may be omitted.

As another example, while a staple applying assembly 20 is illustrated herein, it should be appreciated that other end effectors (graspers, cutting devices, etc.) may benefit from either or both of fluid controlled closing and medical substance dispensing.

As yet another example, a receptacle for the EAP syringe may be formed in the handle rather than in the elongate shaft.

As yet an additional example, a symmetric arrangement for a second EAP syringe may be formed in the elongate channel so that two medical substances may be simultaneously dispensed during firing.

As yet a further example, while a staple applying apparatus provides an illustrative embodiment, it should be appreciated that other endoscopic instruments may benefit from the ability to dispense a liquid at or near a distal end thereof. Examples of instruments that may benefit include, but are not limited to, an ablation device, a grasper, a cauterizing tool, an anastomotic ring introduction device, a surgical stapler, a linear stapler, etc. As such, those instruments that do not employ a firing bar that serves herein as a convenient fluid passage to a cutting surface may instead incorporate ducting or fluid conduits to an appropriate location.

While an electroactive polymer plunger has various advantages, it should be appreciated that other types of electrically actuated devices may be employed to dispense a medical substance through the elongate shaft to the end effector.

What is claimed is:

1. A surgical instrument, comprising:
a handle operably configured to produce a firing motion;
an elongate shaft attached to the handle;
an end effector distally attached to the elongate shaft and comprising opposing jaws for clamping tissue;
a firing member comprising a firing bar received for reciprocating longitudinal motion in the elongate shaft to transfer the firing motion, a cutting surface distally attached to the firing bar to sever the clamped tissue in the end effector, and a fluid passage defined longitudinally in the firing bar to the cutting surface, such that the fluid passage is configured to reciprocate longitudinally with the firing bar and unitarily with the firing bar, wherein the firing bar comprises a longitudinal laminate of a left half and a right half, wherein the fluid passage is defined by a groove formed in the left half and a complementary groove formed in the right half, such that the fluid passage is a unitary feature of the firing bar and such that at least part of the fluid passage extends through at least part of the elongate shaft, wherein the fluid passage is configured to communicate a fluid from a location proximal to the end effector to the cutting surface;
control circuitry operably configured to respond to a firing condition to generate a dispensing signal; and
an electrical fluid dispenser, wherein the electrical fluid dispenser is located proximal to the end effector, wherein the electrical fluid dispenser is in communication with the fluid passage and responsive to the dispensing signal to dispense a medical substance along the fluid passage to the cutting surface, wherein the electrical fluid dispenser further comprises an electroactive polymer actuator.

2. The surgical instrument of claim 1, wherein the electrical fluid dispenser comprises a cylinder partially filled with the medical substance and including a plunger comprising the electroactive actuator operatively configured to extend the plunger into a portion of the cylinder filled with the medical substance.

3. The surgical instrument of claim 2, further comprising an exteriorly accessible receptacle operatively configured to receive a filled cylinder and to extract a spent cylinder.

4. The surgical instrument of claim 2, wherein the cylinder is positioned in the elongate shaft.

5. The surgical instrument of claim 1, wherein the end effector comprises a staple applying assembly.

6. The surgical instrument of claim 1, wherein the electrical fluid dispenser further comprises a reservoir containing the medical substance selected from a group consisting of an anesthetic, an adhesive, a cauterizing substance, an antibiotic substance, and a coagulant.

7. A surgical instrument, comprising:
a handle portion operable to produce a firing motion;
an elongate shaft having a distal portion and a proximal portion, wherein the proximal portion of the elongate shaft is coupled with the handle portion;
an end effector coupled with the distal portion of elongate shaft, the end effector comprising opposing jaws operable to clamp tissue;
a firing member comprising a firing bar disposed in the elongate shaft, wherein the firing bar is operable to longitudinally translate within the elongate shaft to distally transfer the firing motion from the handle to the end effector, wherein the firing member further includes a cutting blade and a fluid passage extending longitudinally along the firing bar such that the fluid passage is configured to translate longitudinally with the firing bar and unitarily with the firing bar in the same direction as the firing bar relative to the elongate shaft, wherein the fluid passage is configured to distally communicate a fluid from a location proximal to the end effector to a location adjacent to the blade as the firing bar and the fluid passage translate unitarily and distally relative to the elongate shaft; and an electrical fluid dispenser, wherein the electrical fluid dispenser is located proximal to the end effector, wherein the electrical fluid dispenser is in communication with the fluid passage, wherein the electrical fluid dispenser is operable to dispense a medical substance along the fluid passage to the location adjacent to the blade.

8. The surgical instrument of claim 7, further comprising a frame extending longitudinally in the elongate shaft, wherein the firing member is slidably disposed in the frame such that the firing member is operable to translate longitudinally relative to the frame.

9. The surgical instrument of claim 8, wherein the fluid passage comprises a groove extending longitudinally along an exterior surface of the firing member.

10. The surgical instrument of claim 9, wherein the fluid passage is further defined in part by a portion of the frame adjacent to the groove of the firing member.

11. The surgical instrument of claim 7, wherein the firing bar comprises a pair of adjacent elongate members, wherein the pair of adjacent elongate members are operable to longitudinally translate together within the elongate shaft to distally transfer the firing motion from the handle.

12. The surgical instrument of claim 11, wherein each elongate member of the pair of adjacent elongate members comprises a respective internal groove, wherein the internal grooves are positioned and configured to together form the fluid passage.

13. A surgical instrument, comprising:
a handle portion;
an elongate shaft extending distally from the handle portion;
an end effector positioned at a distal portion of the elongate shaft, the end effector comprising opposing jaws operable to clamp tissue;
a firing bar disposed in the elongate shaft, wherein the firing bar comprises a first half laminated with a second half, wherein the first half includes a first channel portion, wherein the second half includes a second channel portion complementing the first channel portion, wherein the first and second channel portions together define a longitudinally extending fluid passage, wherein the firing bar is operable to longitudinally translate within the elongate shaft to actuate the end effector, wherein the firing member further includes a cutting blade, wherein at least part of the fluid passage is configured to translate longitudinally with the firing bar, such that at least part of the fluid passage translates longitudinally within the elongate shaft at a location proximal to the end effector, wherein the fluid passage is configured to distally communicate a fluid from a location proximal to the end effector to a location adjacent to a region between the jaws; and
a fluid dispenser, wherein the fluid dispenser is located proximal to the end effector, wherein the fluid dispenser is in communication with the fluid passage, wherein the fluid dispenser is operable to dispense a medical substance along the fluid passage to the region between the jaws.

14. The surgical instrument of claim 13, further comprising an E-beam positioned at a distal end of the firing bar.

15. The surgical instrument of claim 14, wherein the E-beam comprises the blade.

16. The surgical instrument of claim 15, wherein the E-beam further comprises a channel in fluid communication with the fluid passage.

17. The surgical instrument of claim 16, wherein the channel is located adjacent to the blade.

* * * * *